(12) United States Patent
Penthala et al.

(10) Patent No.: US 9,884,842 B2
(45) Date of Patent: Feb. 6, 2018

(54) COMBRETASTATIN ANALOGS

(71) Applicant: The Board of Trustees of the University of Arkansas, Little Rock, AR (US)

(72) Inventors: Narsimha Reddy Penthala, Little Rock, AR (US); Peter Crooks, Little Rock, AR (US); Vijayakumar Sonar, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 0 days.

(21) Appl. No.: 14/785,381

(22) PCT Filed: Apr. 15, 2014

(86) PCT No.: PCT/US2014/034185
§ 371 (c)(1),
(2) Date: Oct. 19, 2015

(87) PCT Pub. No.: WO2014/172363
PCT Pub. Date: Oct. 23, 2014

(65) Prior Publication Data
US 2016/0068506 A1 Mar. 10, 2016

Related U.S. Application Data

(60) Provisional application No. 61/814,028, filed on Apr. 19, 2013, provisional application No. 61/866,878, filed on Aug. 16, 2013, provisional application No. 61/901,710, filed on Nov. 8, 2013.

(51) Int. Cl.
| | | |
|---|---|---|
| C07D 333/60 | (2006.01) |
| C07D 209/18 | (2006.01) |
| C07D 215/14 | (2006.01) |
| C07D 277/64 | (2006.01) |
| C07D 307/79 | (2006.01) |
| C07D 307/80 | (2006.01) |

(52) U.S. Cl.
CPC ......... *C07D 333/60* (2013.01); *C07D 209/18* (2013.01); *C07D 215/14* (2013.01); *C07D 277/64* (2013.01); *C07D 307/79* (2013.01); *C07D 307/80* (2013.01)

(58) Field of Classification Search
CPC .. C07D 333/60; C07D 209/18; C07D 215/14; C07D 277/64; C07D 307/79; C07D 307/80
USPC ........................................................ 514/311
See application file for complete search history.

(56) References Cited

U.S. PATENT DOCUMENTS

| | | | |
|---|---|---|---|
| 3,642,813 A | 2/1972 | Kirchmayr et al. |
| 5,484,940 A | 1/1996 | Grant et al. |
| 9,597,316 B2 | 3/2017 | Penthala et al. |
| 2004/0248950 A1 | 12/2004 | Ishizuka et al. |
| 2007/0238699 A1 | 10/2007 | Demko et al. |
| 2008/0113993 A1 | 5/2008 | De Belin et al. |
| 2009/0253656 A1 | 10/2009 | Yamazaki et al. |
| 2010/0081678 A1 | 4/2010 | Crooks et al. |
| 2010/0144734 A1 | 6/2010 | Hou et al. |
| 2011/0053941 A1 | 3/2011 | Mautino et al. |
| 2011/0077250 A1* | 3/2011 | Ryder .................... A61K 31/70 514/236.8 |
| 2011/0144139 A1 | 6/2011 | Vasioukhin et al. |
| 2011/0251236 A1 | 10/2011 | Lai et al. |
| 2015/0328216 A1 | 11/2015 | Penthala et al. |
| 2016/0075689 A1 | 3/2016 | Penthala et al. |
| 2017/0015635 A1 | 1/2017 | Madadi et al. |

FOREIGN PATENT DOCUMENTS

| | | |
|---|---|---|
| DE | 1944419 A1 | 3/1971 |
| DE | 3410700 A1 | 9/1985 |
| EP | 0754682 A1 | 1/1997 |
| EP | 1921072 A1 | 5/2008 |
| JP | 2012208173 A * | 10/2012 |
| WO | 92/04334 A1 | 3/1992 |
| WO | 199204334 A1 | 3/1992 |
| WO | 0035865 A2 | 6/2000 |
| WO | 0193841 A2 | 12/2001 |
| WO | 2003042207 A1 | 5/2003 |
| WO | 2008131320 A1 | 10/2008 |
| WO | 2010150211 A2 | 12/2010 |
| WO | 2011127192 A2 | 10/2011 |
| WO | 2014/105957 A1 | 7/2014 |
| WO | 2014/172363 A2 | 10/2014 |
| WO | 2014/176351 A1 | 10/2014 |
| WO | 2015/153635 A1 | 10/2015 |

OTHER PUBLICATIONS

Magarian et al. Journal of Pharmaceutical Sciences, 1969, 58(9) 1166-1167.*
Mekouar et al. Journal of Medicinal Chemistry, 1998, 41, 2846-2857.*
Mali et al. Green Chemistry Letters and Reviews, 2010, 3(3), 209-212.*
JP 2012208173 (published Oct. 2012) A machine translation.*
Nhuyen et al. Bioorganic & Medicinal Chemistry Letters, 2012, 22, 7227-7231.*
Haldar et al., "Synthesis of barbiturate-based methionine aminopeptidase-1 inhibitors", Bioorganic & Medicinal Chemistry Letters, 2008, pp. 2373-2376, vol. 18.
International Search Report and Written Opinion from related International Application No. PCT/US2015/023628, dated Aug. 25, 2015, 11 pgs.
International Search Report and Written Opinion from related International Application No. PCT/US2014/34185, dated Nov. 7, 2014, 13 pgs.
International Search Report and Written Opinion from related International Application No. PCT/US2014/035169, dated Sep. 11, 2014, 7 pgs.

(Continued)

*Primary Examiner* — Yevegeny Valenrod
(74) *Attorney, Agent, or Firm* — Polsinelli PC

(57) ABSTRACT

The present invention relates novel heterocyclic analogs of combretastatin, their synthesis, and their use as anti-cancer compounds. In particular, compounds of Formula (I), Formula (II), and Formula (V) are provided.

2 Claims, 13 Drawing Sheets

(56) References Cited

OTHER PUBLICATIONS

International Search Report and Written Opinion from related International Application No. PCT/US2013/77812, dated Apr. 22, 2014, 10 pgs.
Kaur et al., "N-1 and C-3 substituted indole Schiff bases as selective COX-2 inhibitors: Synthesis and biological evaluation", Bioorganic & Medicinal Chemistry Letters, 2012, pp. 2154-2159, vol. 22.
Penthala et al., "Synthesis and In Vitro Screening of Novel Heterocyclic Compounds as Potential Breast Cancer Agents", cited on www.intechopen.com, 2011, pp. 283-295.
Penthala et al., "Synthesis and evaluation of a series of benzothiophene acrylonitrile analogs as anticancer agents", Medchemcomm., 2013, pp. 1073-1078, vol. 4, No. 7.
PubChem, Compound Summary, Chemicals & Bioassays, National Center for Biotechnology Information, 2005, 4 pages.
Singh et al., "Design, synthesis and anticancer activities of hybrids of indole and barbituric acids—Identification of highly promising leads", Bioorganic & Medicinal Chemistry Letters, 2009, pp. 3054-3058, vol. 19.
Bhatnagar, I. et al., "Oxidation of Phenylhydrazones with Manganese Dioxide," J. Org. Chem., Jul. 1967, pp. 2252-2256, vol. 32.
Grundon, M. et al., "The Reactions of Hydrazones and Related Compounds with Strong Bases. Part 4. 4,5-Diaryl-1,2,3-triazoles from Aromatic Aldehyde Azines and from the Reaction of Arenecarbonitriles with Aryldiazomethanes," J. Chem. Soc. Perkin Trans. I, 1988, pp. 2917-2919, vol. 1.
Khadem, H. et al., "Reactions of Benzil Mono- and Bisarylhydrazones," J. Chem. Soc., Jan. 1, 1968, pp. 949-951, vol. 8.
Office Action dated May 9, 2017 from related U.S. Appl. No. 15/282,312; 14 pgs.
Carta, A. et al., "3-Aryl-2-[1H-benzotriazol-1-yl]acrylonitriles: A novel class of potent tubulin inhibitors," Eur. J. Med. Chem., Jun. 11, 2011, pp. 4151-4167, vol. 46, No. 9, Elsevier Masson SAS, Paris, France.
Coggins, G. et al., "N-Aroyl Indole Thiobarbituric Acids as Inhibitors of DNA Repair and Replication Stress Response Polymerases," NIH Public Access, Author Manuscript, available in PMC Aug. 16, 2014, pp. 1-19, published in final edited form as: ACS Chem Biol., Aug. 16, 2013, pp. 1722-1729, vol. 8, No. 8.
Corrected Search Report and Written Opinion dated Oct. 12, 2016 from related Singaporean Patent Application No. 11201508054U; 11 pgs.
Dhayalan, V. et al., "Studies on Lewis-acid mediated domino reaction of N-protected bromomethylindoles with arenes/heteroarenes," Indian Journal of Chemistry, Jun. 2011, pp. 843-857, vol. 50B.
Extended European Search Report dated May 12, 2016 from related European Patent Application No. 13868363.6; 6 pgs.
Extended European Search Report dated Jan. 12, 2017 from related European Patent Application No. 14785256.0; 14 pgs.
Extended European Search Report dated Oct. 18, 2016 from related European Patent Application No. 14788020.7; 12 pgs.
Jalily, P. et al., "Novel cyanocombretastatins as potent tubulin polymerization inhibitors," Bioorg. Med. Chem. Lett., Sep. 7, 2012, pp. 6731-6734, vol. 22, No. 21, Elsevier Ltd.
Kubinyi, E., "3D QSAR in Drug Design Theory Methods and Applications: Ligand-Protein Interactions and Molecular Similarity," Springer, 1998, pp. 243-244, vol. 2-3.
Madadi, N. et al., "Synthesis and anti-proliferative activity of aromatic substituted 5-((1-benzyl-1H-indol-3-yl) methylene)-1,3-dimethylpyrimidine-2,4,6(1H,3H,5H)-trione analogs against human tumor cell lines," NIH Public Access, Author Manuscript, available in PMC Jan. 15, 2015, pp. 1-10, Published in final edited form as: Bioorg. Med. Chem. Lett., Jan. 15, 2014, pp. 601-603, vol. 24, No. 2, Elsevier Ltd.
Maya, A. et al., "Further Naphthylcombretastatins. An Investigation on the Role of the Naphthalene Moiety," J. Med. Chem., 2005, pp. 556-568, vol. 48, No. 2, American Chemical Society, United States.
Nguyen, T. et al., "Synthesis of (Z) isomers of benzoheterocyclic derivatives of combretastatin A-4: a comparative study of several methods," Tetrahedron, Jan. 9, 2013, pp. 2336-2347, vol. 69, No. 10, Elsevier Science Publishers, Amsterdam, Netherlands.
Notice of Allowance dated Dec. 1, 2016 from related U.S. Appl. No. 14/651,113; 5 pgs.
Office Action dated Jun. 3, 2016 from related U.S. Appl. No. 14/651,113; 9 pgs.
Office Action dated Jul. 6, 2016 from related Canadian Patent Application No. 2,910,063; 4 pgs.
Office Action dated Nov. 17, 2016 from related U.S. Appl. No. 14/786,331; 15 pgs.
Ohsumi, K et al., "Novel Combretastatin Analogues Effective against Murine Solid Tumors: Design and Structure-Activity Relationships," J. Med. Chem., Sep. 7, 1998, pp. 3022-3032, vol. 41, No. 16, American Chemical Society, United States.
Penthala, N. et al., "5-((1-Aroyl-1H-indol-3-yl)methylene)-2-thioxodihydropyrimidine-4,6(1H,5H)-diones as potential anticancer agents with anti-inflammatory properties," Bioorg. Med. Chem. Lett., Mar. 1, 2013, pp. 1442-1446, vol. 23, No. 5, Elsevier Ltd.
Penthala, N. et al., "5((1-Aroyl-1H-indol-3-yl)methylene)-2-thioxodihydropyrimidine-4,6(1H,5H)-diones as potential anticancer agents with anti-inflammatory properties," NIH Public Access, Author Manuscript, available in PMC Sep. 18, 2014, pp. 1-14, Elsevier Ltd.; Published in final edited form as: Bioorg. Med. Chem. Lett., Mar. 1, 2013, pp. 1442-1446, vol. 23, No. 5.
Penthala, N. et al., "(Z)-3-(1H-indol-3-yl)-2-(3,4,5-trimethoxyphenyl)acrylonitrile," Acta Crystallographica Section E, Feb. 17, 2012, p. o729, vol. E68, with Supporting Information, pp. sup1-sup7.
Perez-Melero, C. et al., "A new family of quinolone and quinoxaline analogues of combretastatins," Bioorg. Med. Chem. Lett., May 25, 2004, pp. 3771-3774, vol. 14, Elsevier Ltd.
Reddy, Y. et al., "Novel substituted (Z)-5-((N-benzyl-1H-indol-3-yl)methylene)imidazolidine-2,4-diones and 5-((N-benzyl-1H-indol-3-yl)methylene)pyrimdine-2,4,6(1H,3H,5H)-triones as potent radio-sensitizing agents," Bioorg. Med. Chem. Lett., Jan. 15, 2010, pp. 600-602, vol. 20, No. 2, Elsevier Ltd.
Saczewski, F. et al., "Synthesis, X-ray Crystal Structures, Stabilities, and in Vitro Cytotoxic Activities of New Heteroarylacrylonitriles," J. Med. Chem., 2004, pp. 3438-3449, vol. 47, No. 13, American Chemical Society.
Sekhar, K. et al., "The novel chemical entity YTR107 inhibits recruitment of nucleophosmin to sites of DNA damage, suppressing repair of DNA double strand breaks, and enhancing radiosensitization," NIH Public Access, Author Manuscript, available in PMC Oct. 15, 2012, pp. 1-18, published in final edited form as: Clin. Cancer Res., Oct. 15, 2011, pp. 6490-6499, vol. 17, No. 20.
Shaveta, P. et al., "Structural optimization of indole based compounds for highly promising anti-cancer activities: Structure activity relationship studies and identification of lead molecules," European Journal of Medicinal Chemistry, Jan. 8, 2014, pp. 440-450, vol. 74.
Sonar, V. et al., "(E)-3-(Benzo[b]thiophen-2-yl)-2-(3,4,5-trimethoxyphenyl)acrylonitrile and (Z)-3-(benzo[b]thiophen-2-yl)-2-(3,4-dimethoxyphenyl)acrylonitrile," Acta Crystallographica Section C, Nov. 24, 2007, pp. o743-o745, vol. C63, International Union of Crystallography.
Supplementary Partial Search Report dated Oct. 6, 2016 from related European Patent Application No. 14785256.0; 8 pgs.
Wermuth, "The Practice of Medicinal Chemistry," 2d. Ed., 2003, Chapters 9-10, pp. 131-157, Elsevier.
Butler et al., A ceric ammonium nitrate N-dearylation of N-p-anisylazoles applied to pyrazole, triazole, tetrazole, and pentazole rings: release of parent azoles. generation of unstable pentazole, HN5/N5-, in solution, J Org Chem, 2008, vol. 73, No. 4, pp. 1354-1364.
Database Pubchem, Compound Summary for CID 613500.
European Search Report and Written Opinion, related to Application No. 15773146.4, dated Aug. 3, 2017, 13 pages.
Hou et al., "1, 2, 3-Triazole derivatives as new cannabinoid CB1 receptor antagonists," Bioorganic & Medicinal Chemistry Letters, 2009, vol. 19, No. 3, pp. 1022-1025.

(56) References Cited

OTHER PUBLICATIONS

Hu et al., "A one-pot synthesis of bisarylhydrazones by Cu(I)-catalyzed aerobic oxidation," Tetrahedron, 2013, vol. 69, No. 46, pp. 9865-9869.

Kim et al., "Synthesis and biological evaluation of novel 2-pyridinyl-[1,2,3] triazoles as inhibitors of transforming growth factor @b1 type 1 receptor," Bioorganic & Medicinal Chemistry Let, 2004, vol. 14, No. 10, pp. 2401-2405.

Madadi et al., "Preparation of 4,5 disubstituted-2H-1,2,3-triazoles from (Z)-2,3-diaryl substituted acrylonitriles," Tetrahedron Letters, 2014, vol. 55, No. 30, pp. 4207-4211.

Odlo et al., "1,5-Disubstituted 1,2,3-triazoles as cis-restricted analogues of combretastatin A-4: Synthesis, molecular modeling and evaluation as cytotoxic agents and inhibitors of tubulin," Bioorganic & Medicinal Chemistry, 2008, vol. 16, No. 9, pp. 4829-4838.

Ohsumi et al., "Syntheses and antitumor activity of cis-restricted combretastatins: 5-Membered heterocyclic analogues," Bioorganic & Medicinal Chemistry Letters, 1998, vol. 8, Issue 22, pp. 3153-3158.

Oliva et al., "N-Substituted-1,2,3-triazoles: synthesis, characterization and evaluation as cannabinoid ligands," Arkivoc, 2010, vol. 2 pp. 127-147.

Papudippu et al., "Regioselective synthesis and cannabinoid receptor binding affinity of N-alkylated 4,5-diaryl-1,2,3- triazoles," Medicinal Chemistry Research, 2012, vol. 21, Issue 12, pp. 4473-4484.

Romagnoli et al., "Synthesis and Antitumor Activity of 1,5-Disubstituted 1,2,4-Triazoles as Cis-Restricted Combretastatin Analogues," Journal of Medicinal Chemistry, 2010, vol. 53, No. 10, pp. 4248-4258.

Tome, "Product Class 13: 1, 2, 3-Triazoles," Science of Synthesis, 2004, vol. 13, No. 2, pp. 429-470.

Wang et al., "General Solution to the Synthesis of N-2-Substituted 1,2,3-Triazoles," Organic Letters, 2010, vol. 12, No. 20 pp. 4632-4635.

* cited by examiner

A

R⁶=H, or CN
R⁸=R¹⁰=OCH₃, R⁹=H
R⁸=R¹⁰=H, R⁹=OCH₃
R⁸=R⁹=OCH₃, R¹⁰=H
R⁸=R⁹=R¹⁰=OCH₃
R⁸=R¹⁰=OCH₃, R⁹=OH
R⁸=R¹⁰=H, R⁹=OH

B

R⁶=H, or CN
R⁸=R⁹=OCH₃, R¹⁰=H
R⁸=R¹⁰=OCH₃, R⁹=H
R⁸=R¹⁰=H, R⁹=OCH₃
R⁸=R⁹=R¹⁰=OCH₃
R⁸=R¹⁰=OCH₃, R⁹=OH
R⁸=R¹⁰=H, R⁹=OH

R⁶=H, or CN
R⁸=R⁹=OCH₃, R¹⁰=H
R⁸=R¹⁰=OCH₃, R⁹=H
R⁸=R¹⁰=H, R⁹=OCH₃
R⁸=R⁹=R¹⁰=OCH₃
R⁸=R¹⁰=OCH₃, R⁹=OH
R⁸=R¹⁰=H, R⁹=OH

A

R⁶=H, or CN
R⁸=R¹⁰=OCH₃, R⁹=H
R⁸=R⁹=OCH₃, R¹⁰=H
R⁸=R¹⁰=H, R⁹=OCH₃
R⁸=R⁹=R¹⁰=OCH₃
R⁸=R¹⁰=OCH₃, R⁹=OH
R⁸=R¹⁰=H, R⁹=OH

B

R⁶=H, or CN
R⁸=R⁹=OCH₃, R¹⁰=H
R⁸=R¹⁰=OCH₃, R⁹=H
R⁸=R¹⁰=H, R⁹=OCH₃
R⁸=R⁹=R¹⁰=OCH₃
R⁸=R¹⁰=OCH₃, R⁹=OH
R⁸=R¹⁰=H, R⁹=OH

C $R^6$=H, or CN
$R^8$=$R^9$=OCH$_3$, $R^{10}$=H
$R^8$=$R^{10}$=OCH$_3$, $R^9$=H
$R^8$=$R^{10}$=H, $R^9$=OCH$_3$
$R^8$=$R^9$=$R^{10}$=OCH$_3$
$R^8$=$R^{10}$=OCH$_3$, $R^9$=OH
$R^8$=$R^{10}$=H, $R^9$=OH

D $R^6$=H, or CN
$R^8$=$R^9$=OCH$_3$, $R^{10}$=H
$R^8$=$R^{10}$=OCH$_3$, $R^9$=H
$R^8$=$R^{10}$=H, $R^9$=OCH$_3$
$R^8$=$R^9$=$R^{10}$=OCH$_3$
$R^8$=$R^{10}$=OCH$_3$, $R^9$=OH
$R^8$=$R^{10}$=H, $R^9$=OH

E $R^8=R^{10}=OCH_3, R^9=H$
$R^8=R^{10}=H, R^9=OCH_3$
$R^8=R^{10}=OCH_3, R^9=OH$
$R^8=R^{10}=H, R^9=OH$

F $R^8=R^9=OCH_3, R^{10}=H$
$R^8=R^{10}=OCH_3, R^9=H$
$R^8=R^{10}=H, R^9=OCH_3$
$R^8=R^{10}=OCH_3, R^9=OH$
$R^8=R^{10}=H, R^9=OH$

G

$R^6$ = H or CN
$R^8 = R^9 = OCH_3$, $R^{10}$ = H
$R^8 = R^{10} = OCH_3$, $R^9$ = H
$R^8 = R^{10}$ = H, $R^9 = OCH_3$
$R^8 = R^{10} = OCH_3$, $R^9$ = OH
$R^8 = R^{10}$ = H, $R^9$ = OH

H

$R^6$ = H or CN
$R^8 = R^9 = OCH_3$, $R^{10}$ = H
$R^8 = R^{10} = OCH_3$, $R^9$ = H
$R^8 = R^{10}$ = H, $R^9 = OCH_3$
$R^8 = R^9 = R^{10} = OCH_3$
$R^8 = R^{10} = OCH_3$, $R^9$ = OH
$R^8 = R^{10}$ = H, $R^9$ = OH

I

$R^8=R^{10}=OCH_3$, $R^9=H$
$R^8=R^{10}=H$, $R^9=OCH_3$
$R^8=R^9=R^{10}=OCH_3$
$R^8=R^{10}=OCH_3$, $R^9=OH$
$R^8=R^{10}=H$, $R^9=OH$

J

$R^8=R^9=OCH_3$, $R^{10}=H$
$R^8=R^{10}=OCH_3$, $R^9=H$
$R^8=R^{10}=H$, $R^9=OCH_3$
$R^8=R^9=R^{10}=OCH_3$
$R^8=R^{10}=OCH_3$, $R^9=OH$
$R^8=R^{10}=H$, $R^9=OH$ $R^8=R^9=OCH_3$, $R^{10}=H$
$R^8=R^{10}=OCH_3$, $R^9=H$
$R^8=R^{10}=H$, $R^9=OCH_3$
$R^8=R^9=R^{10}=OCH_3$
$R^8=R^{10}=OCH_3$, $R^9=OH$
$R^8=R^{10}=H$, $R^9=OH$

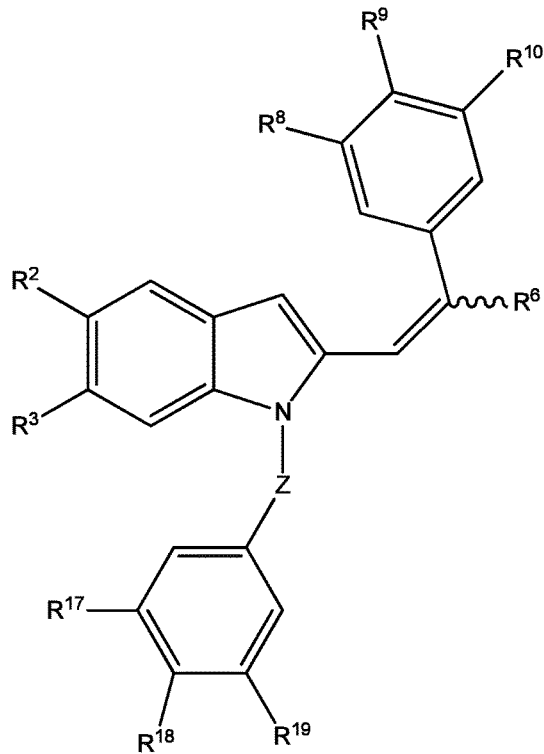

Z=CH$_2$, CO, SO$_2$

R$^6$=H, or CN
R$^8$=R$^9$=OCH$_3$, R$^{10}$=H
R$^8$=R$^{10}$=OCH$_3$, R$^9$=H
R$^8$=R$^{10}$=H, R$^9$=OCH$_3$
R$^8$=R$^9$=R$^{10}$=OCH$_3$
R$^8$=R$^{10}$=OCH$_3$, R$^9$=OH
R$^8$=R$^{10}$=H, R$^9$=OH

R$^2$=H, CH$_3$, CN, CF$_3$, COOH, COOCH$_3$, F, Cl, Br, I, NH$_2$
R$^3$=H, CH$_3$, CN, CF$_3$, COOH, COOCH$_3$, F, Cl, Br, I, NH$_2$
R$^{17}$=H, CH$_3$, CN, CF$_3$, COOH, COOCH$_3$, F, Cl, Br, I, NH$_2$
R$^{18}$=H, CH$_3$, CN, CF$_3$, COOH, COOCH$_3$, F, Cl, Br, I, NH$_2$
R$^{19}$=H, CH$_3$, CN, CF$_3$, COOH, COOCH$_3$, F, Cl, Br, I, NH$_2$

$R^6$=H, or CN
$R^8=R^9$=OCH₃, $R^{10}$=H
$R^8=R^{10}$=OCH₃, $R^9$=H
$R^8=R^{10}$=H, $R^9$=OCH₃
$R^8=R^9=R^{10}$=OCH₃
$R^8=R^{10}$=OCH₃, $R^9$=OH
$R^8=R^{10}$=H, $R^9$=OH $R^2$=H, CH₃, CN, CF₃, COOH, COOCH₃, F, Cl, Br, I, NH₂
$R^3$=H, CH₃, CN, CF₃, COOH, COOCH₃, F, Cl, Br, I, NH₂
$R^{17}$=H, CH₃, CN, CF₃, COOH, COOCH₃, F, Cl, Br, I, NH₂
$R^{18}$=H, CH₃, CN, CF₃, COOH, COOCH₃, F, Cl, Br, I, NH₂
$R^{19}$=H, CH₃, CN, CF₃, COOH, COOCH₃, F, Cl, Br, I, NH₂

R⁶=H or CN
R⁸=R¹⁰=OCH₃, R⁹=H
R⁸=R¹⁰=H, R⁹=OCH₃
R⁸=R⁹=R¹⁰=OCH₃
R⁸=R¹⁰=OCH₃, R⁹=OH
R⁸=R¹⁰=H, R⁹=OH
R⁸=R¹⁰=Cl, R⁹=H
R⁸=R⁹=Cl, R¹⁰=H
R⁸=R¹⁰=H, R⁹=Cl
R⁸=R¹⁰=H, R⁹=CF₃
R⁸=CF₃, R⁹=R¹⁰=H

COMBRETASTATIN ANALOGS

CROSS-REFERENCE TO RELATED APPLICATIONS

This application claims the benefit of PCT Application PCT/US2014/034185, filed Apr. 15, 2014, which claims the benefit of U.S. Provisional Patent Application No. 61/814,028, filed Apr. 19, 2013, U.S. Provisional Patent Application No. 61/866,878, filed Aug. 16, 2013, and U.S. Provisional Patent Application No. 61/901,710 filed Nov. 8, 2013, which are each hereby incorporated by reference in their entirety.

FIELD

The present invention relates novel analogs of combretastatin, their synthesis, and their use as anti-cancer compounds.

BACKGROUND

The isolation of stilbene derivatives, termed combretastatins, from the South African tree *Combretum caffrum* has been described. Many of these combretastatins were found to be cytotoxic, with combretastatin A-4 being the most potent. This compound was found to inhibit tubulin polymerization and to competitively inhibit the binding of radiolabeled colchicines to tubulin. Investigation of combretastatins revealed that combretastatin A-4 was active against multidrug resistant (MDR) cancer cell lines. Combretastatin A-4, as well as its trans isomer and a number of related substances, have been found to cause mitotic arrest in cells in culture at cytotoxic concentrations. trans-Tetrahydroxystilbene and a number of related substances were also reported to be cytotoxic agents.

2,3-Diarylacrylonitriles are also very important synthons for the synthesis of a wide spectrum of biologically active molecules. These compounds have been shown to possess spasmolytic, estrogenic, hypotensive, antioxidative, tuberculostatic, antitrichomonal, insecticidal and cytotoxic activities. Also, many natural products possessing a trimethoxybenzene ring, e.g., colchicines, and podophyllotoxin, were found to be potent cytotoxic agents and exert their antitumor properties based on their antitubulin character.

Although some compounds have shown biological activity, there remains a need for novel compounds for the treatment of disease.

BRIEF DESCRIPTION OF THE DRAWINGS

The application file contains at least one photograph executed in color. Copies of this patent application publication with color photographs will be provided by the Office upon request and payment of the necessary fee.

FIG. 3A and FIG. 3B show N-alkyl indole combretastatin heterocyclic E and Z-isomer analogs.

DETAILED DESCRIPTION

Figure 1:
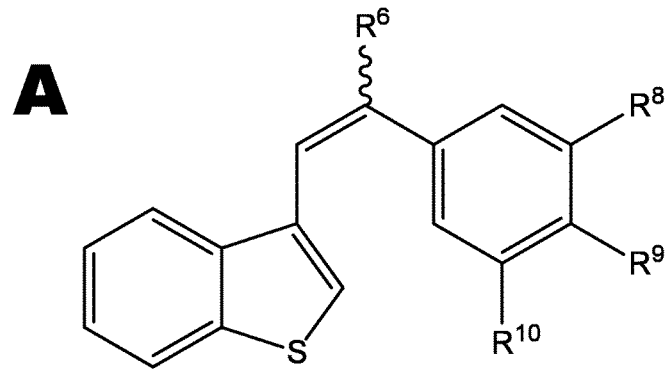
FIG. 1A, FIG. 1B and FIG. 1C show various combretastatin heterocyclic E and Z-isomer analogs.
Figure 1:
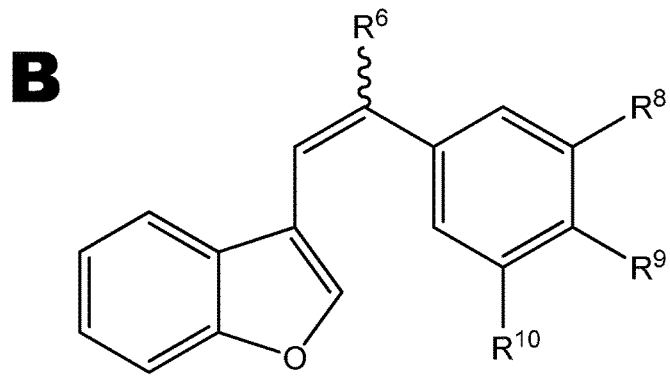
Figure 1C:
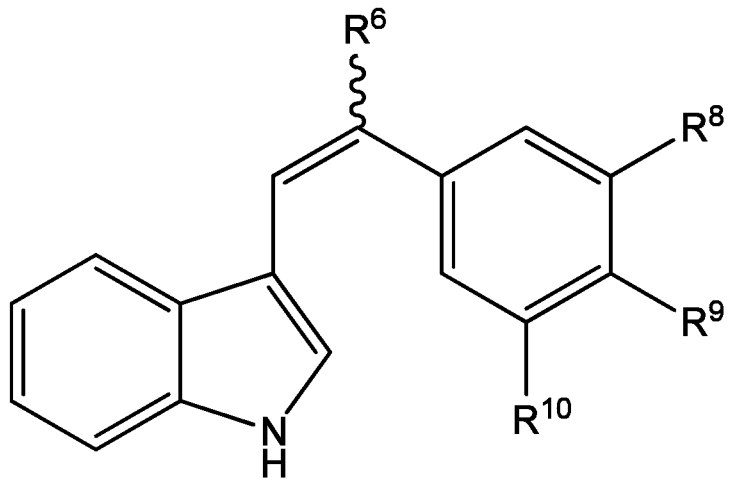

Briefly, the present invention relates to novel heterocyclic combretastatin analogs. The analogs generally have a heterocyclic structural feature and a stilbene (or combretastatin) structural feature, each of which may each be further derivatized. These analogs show novel and unexpected properties in terms of biological activity, and in particular showing cytotoxicity against various cancer cell lines. It is thought that this cytotoxicity is due to the ability of the compound to bind to tubulin and to inhibit tubulin polymerization. Due to this activity, the compounds described herein may be active in the treatment of a variety of diseases including in the treatment of cancer.

I. Compositions (a) Compound Comprising Formula (I)

One aspect of the invention provides compounds comprising Formula (I):

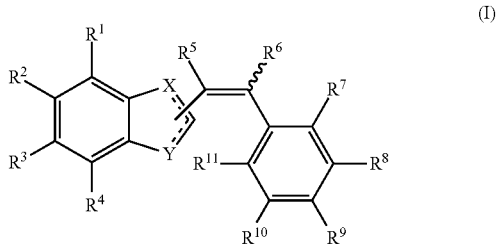

(I)

wherein:
$R^1$, $R^2$, $R^3$, $R^4$, $R^7$, $R^8$, $R^9$, $R^{10}$, $R^{11}$ are independently chosen from hydrogen, hydrocarbyl, substituted hydrocarbyl, alkylalkylamino, amidine, amino, carboxyl, cyano, ester, halogen, hydroxyl, and nitro;

$R^5$ and $R^6$ are independently chosen from hydrogen, hydrocarbyl, substituted hydrocarbyl, carboxyl, ester, and cyano;

X and Y are independently chosen from O, C, $CR^{12}$, $CR^{12}R^{13}$, S, $SR^{14}N$, or $NR^{15}$; and $R^{12}$, $R^{13}$, $R^{14}$, and $R^{15}$ are independently chosen from hydrogen, hydrocarbyl, substituted hydrocarbyl, alkylalkylamino, amidine, amino, carboxyl, cyano, ester, halogen, hydroxyl, and nitro.

$R^1$, $R^2$, $R^3$, and $R^4$ are independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached to the phenyl ring at either the carbonyl end or at the oxygen end of the ester. The opposite terminus may be hydrocarbyl or substituted hydrocarbyl, and is preferably a lower alkyl.

In one embodiment, $R^1$, $R^2$, $R^3$, and $R^4$ are chosen from hydrogen, hydroxyl, and alkoxy. In a preferred embodiment, $R^1$ and $R^4$ are both hydrogen. In yet another preferred embodiment, each of $R^1$, $R^2$, $R^3$, and $R^4$ are hydrogen.

$R^7$, $R^8$, $R^9$, $R^{10}$, and $R^{11}$ are independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached at either the carbonyl end or at the oxygen end of the ester. The opposite terminus of the ester may be hydrocarbyl or substituted hydrocarbyl. Preferably, the ester is a lower alkyl.

In certain embodiments, $R^7$, $R^8$, $R^9$, $R^{10}$, and $R^{11}$ are chosen from hydrogen, hydroxyl, and alkoxy. In one preferred embodiment, $R^7$ and $R^{11}$ are hydrogen.

In another embodiment, $R^8$, $R^9$, and $R^{10}$ are independently chosen from hydrogen, methoxy, ethoxy, benzyloxy, substituted benzyloxy, hydroxyl, and lower alkyl groups. In one embodiment, $R^8$, $R^9$, and $R^{10}$ are independently chosen from hydrogen, hydroxyl, and alkoxy. In one preferred embodiment, $R^8$, $R^9$, and $R^{10}$ are each methoxy, and in still another preferred embodiment, $R^8$ and $R^{10}$ are methoxy, and $R^9$ is hydrogen.

$R^5$ and $R^6$ are independently chosen from hydrogen, hydrocarbyl, substituted hydrocarbyl, carboxyl, ester, and cyano. Ester groups may be attached at either the carbonyl end or at the oxygen end of the ester. The terminus of the ester that is not bound to the double bond may be hydrocarbyl or substituted hydrocarbyl. Preferably, the ester is a lower alkyl ester.

In one embodiment, $R^5$ is hydrogen and $R^6$ is chosen from hydrogen, cyano, and carboxyl. In still another embodiment, $R^5$ is hydrogen and $R^6$ is cyano. In yet another exemplary embodiment, $R^5$ and $R^6$ are hydrogen.

X and Y are independently chosen from O, C, $CR^{12}$, $CR^{12}R^{13}$, S, $SR^{14}N$, and $NR^{15}$. In one embodiment, where X is chosen from C, $CR^{12}$, or $CR^{12}R^{13}$, then Y is not chosen from C, $CR^{12}$, or $CR^{12}R^{13}$. In another embodiment, X is chosen from C or S. In still another embodiment, Y is chosen from O, S, and $NR^{15}$. In some specific embodiments, X is C and Y is S, or X is C and Y is O, or X is C and Y is $NR^{15}$, or X is S and Y is N.

$R^{12}$, $R^{13}$, $R^{14}$, and $R^{15}$ are independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached at either the carbonyl end or at the oxygen end of the ester. The terminus of the ester that is not bound to the aromatic ring may be hydrocarbyl or substituted hydrocarbyl. Preferably, the ester is a lower alkyl.

In one preferred embodiment, each of $R^{12}$, $R^{13}$, $R^{14}$, and $R^{15}$ are hydrogen. In yet another embodiment, $R^{12}$, $R^{13}$, $R^{14}$, and $R^{15}$ comprise the formula:

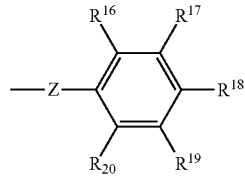

wherein Z is chosen from $CH_2$, CO, and $SO_2$; and $R^{16}$, $R^{17}$, $R^{18}$, $R^{19}$, and $R^{20}$ are independently chosen from hydrogen, hydrocarbyl, substituted hydrocarbyl, alkylalkylamino, amidine, amino, carboxyl, cyano, ester, halogen, hydroxyl, and nitro.

In one preferred embodiment, $R^{16}$ and $R^{20}$ are hydrogen, while $R^{17}$, $R^{18}$, and $R^{19}$ are chosen from amino, carboxyl, cyano, ester, halogen, alkyl, and hydrogen.

The dashed lines in the five-membered ring of the compound comprising Formula (I) indicate either a single bond or a double bond. Preferably, one of the dashed lines represents a single bond, and the other represents a double bond.

The stilbene or modified stilbene moiety may be bonded to the five-membered ring at any one of the non-fused ring positions. In various embodiments, the stilbene moiety may be attached through a bond to X, through a bond to Y, or a bond to the carbon atom between the X and Y atoms.

The wavy bond at $R^6$ indicates that $R^6$ may be at either geometric position on the double bond. Accordingly, the double bond may be (E) or (Z), which are defined according to the IUPAC convention. In one embodiment, the double bond may have an (E) configuration, and in another embodiment, the double bond may have a (Z) configuration.

The compound comprising Formula (I) may be a free form or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents.

In one embodiment, the disclosure provides a compound comprising Formula (I)(a):

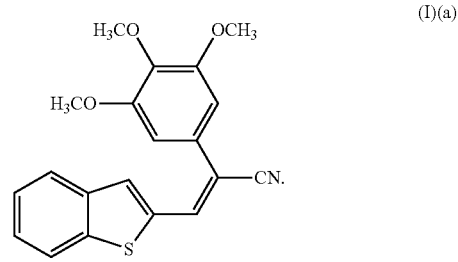 [SMILES: COc1cc(/C(C#N)=C\c2cc3ccccc3s2)cc(OC)c1OC]

In still another embodiment, the disclosure provides a compound comprising Formula (I)(b):

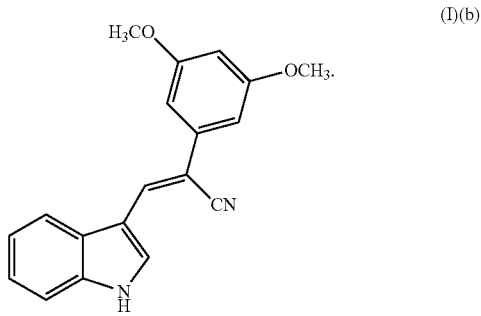 [SMILES: COc1cc(OC)cc(/C(C#N)=C/c2c[nH]c3ccccc23)c1]

In still another embodiment, the disclosure provides a compound comprising Formula (I)(c):

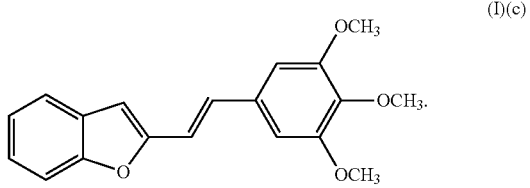 [SMILES: COc1cc(/C=C/c2cc3ccccc3o2)cc(OC)c1OC]

In still a further embodiment, the disclosure provides a compound comprising Formula (I)(d):

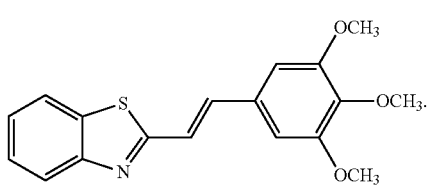

In still a further embodiment, the disclosure provides a compound comprising Formula (I)(e):

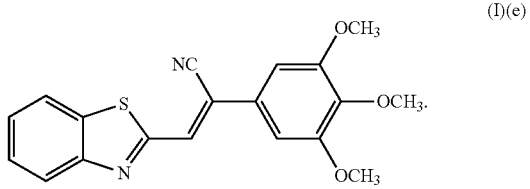 [SMILES: COc1cc(/C(C#N)=C/c2nc3ccccc3s2)cc(OC)c1OC]

Figure 2:
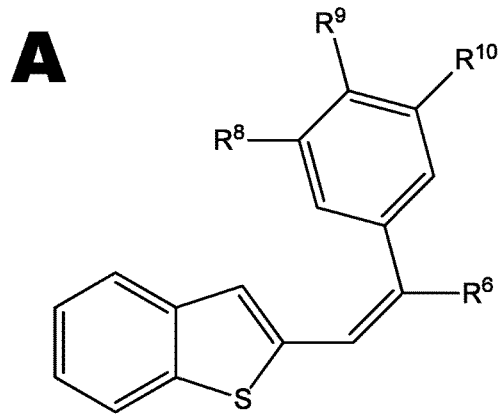
FIG. 2A, FIG. 2B, FIG. 2C, FIG. 2D, FIG. 2E, FIG. 2F, FIG. 2G, FIG. 2H, FIG. 2I, FIG. 2J and FIG. 2K show further combretastatin heterocyclic E and Z-isomer analogs.
Figure 2:
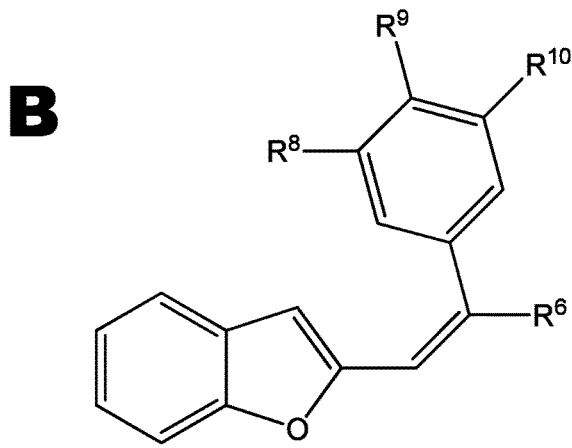
Figure 2:
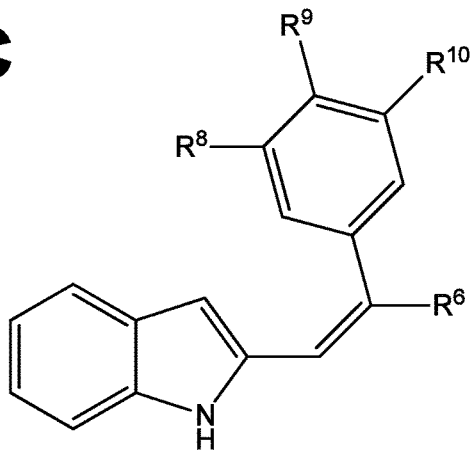
Figure 2:
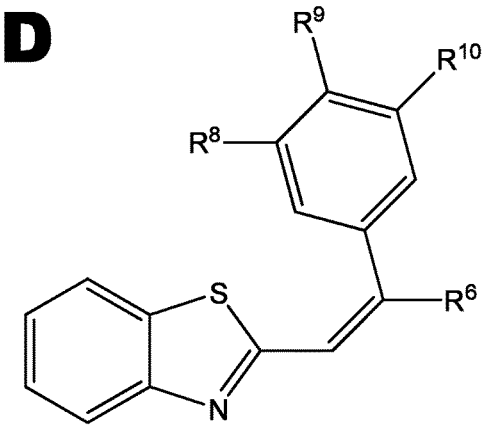
Figure 2:
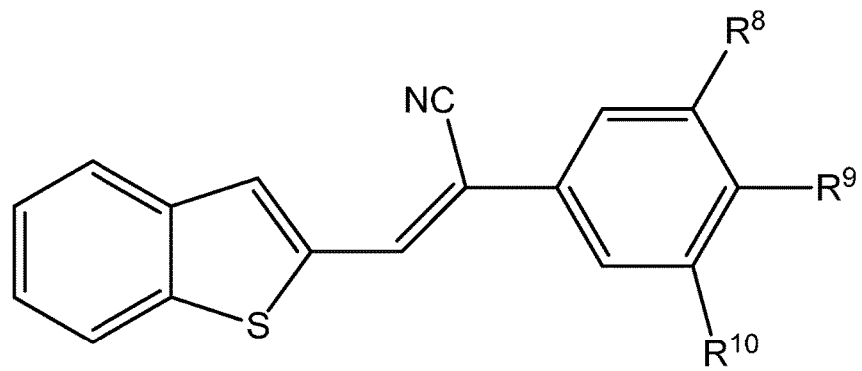
Figure 2:
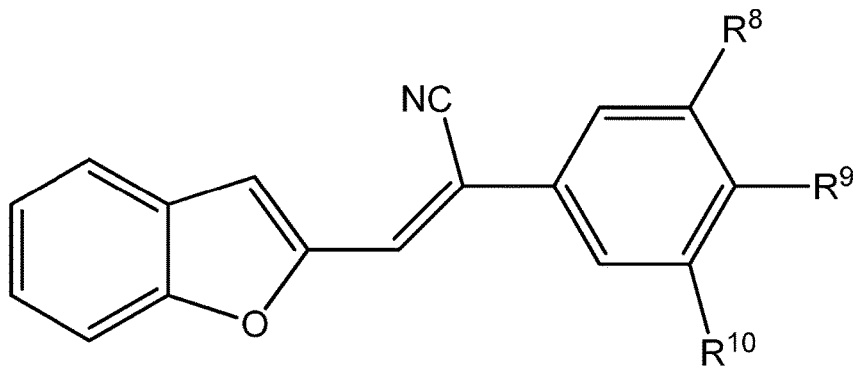
Figure 2:
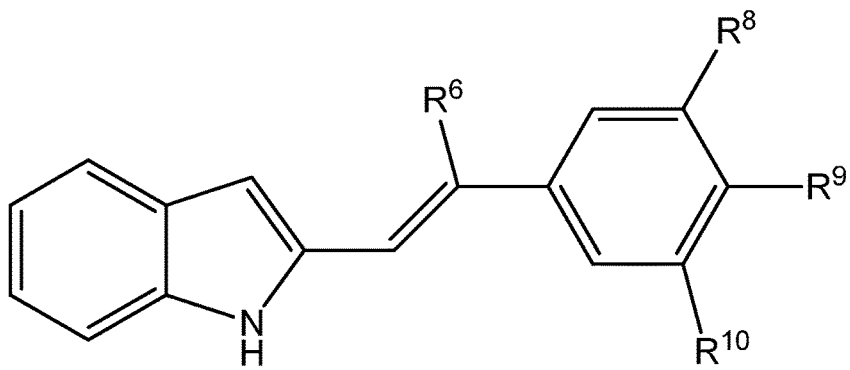
Figure 2:
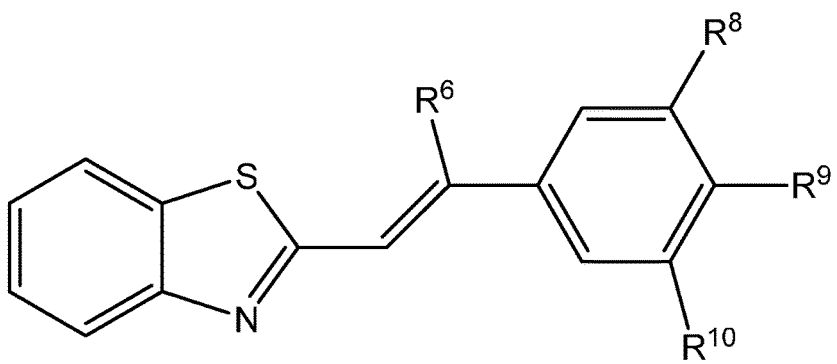
Figure 2:
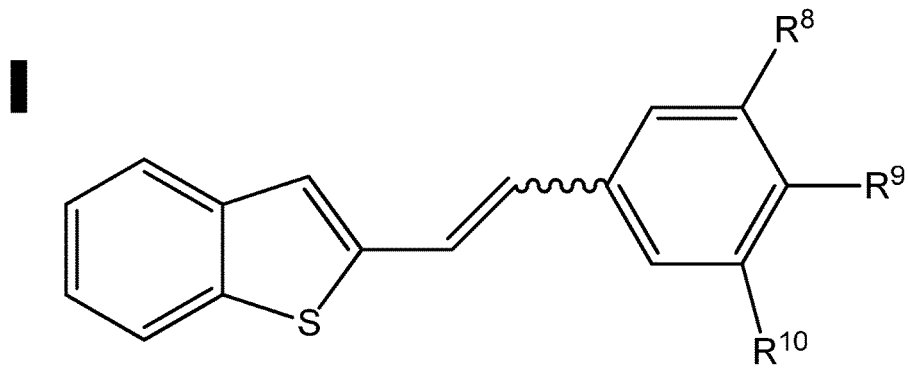
Figure 2:
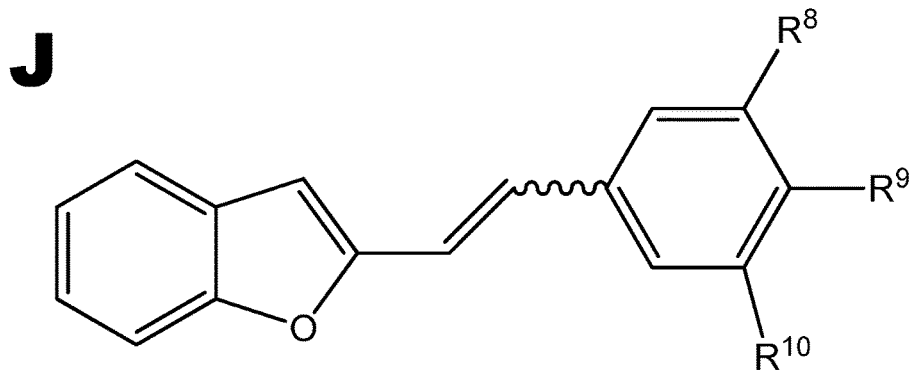
Figure 2K:
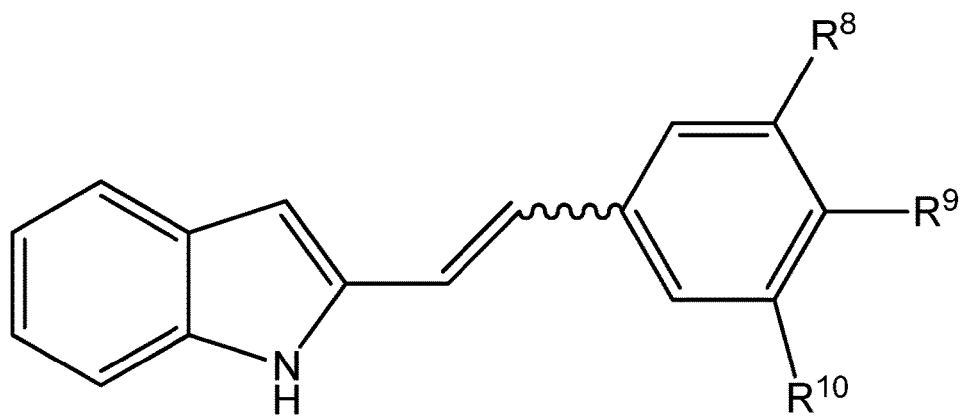
Figure 3B:
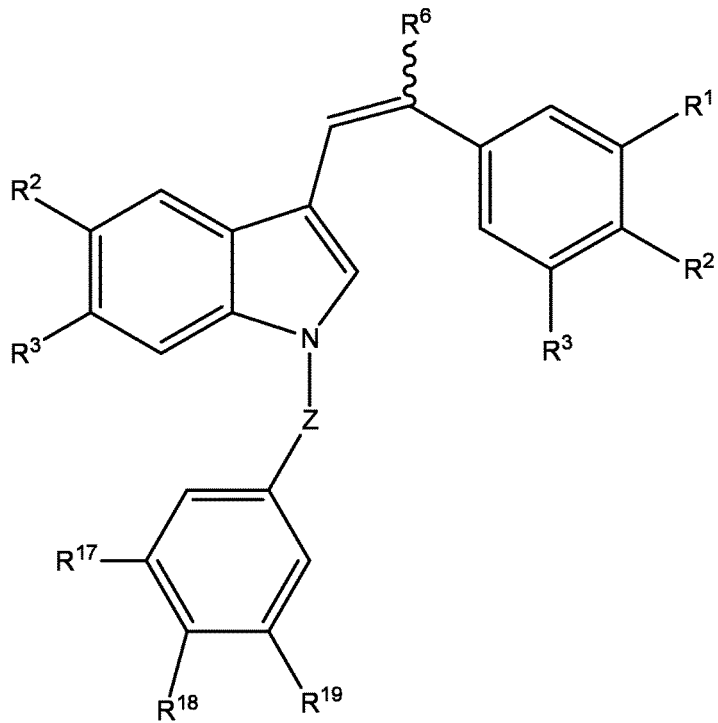

Additional embodiments are shown in FIGS. 1 to 3.

(b) Pharmaceutical Compositions

The disclosure also provides a pharmaceutical composition comprising the compound comprising Formula (I) and at least one pharmaceutically acceptable excipient. In various embodiments, one or more of the compounds described in section (I) may be combined with at least one pharmaceutically acceptable excipient.

(i) Excipient

A pharmaceutical composition of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Buffers may include phosphates, carbonates, citrates, and the like. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate, or EDTA (ethylenediaminetetraacetic acid), EGTA (ethylene glycol tetraacetic acid), BHA (butylated hydroxyanisole), BHT (butylated hydroxytoluene), and the like.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants may include minerals such as talc or silica; and fats such as vegetable stearin, magnesium stearate, or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid, or cream dosage form. Methods of formulating a solid, liquid, or cream dosage form are known in the art.

(ii) Optional Additional Pharmaceutical Ingredient

Optionally, the compound comprising Formula (I) may be combined with other compounds comprising Formula (I) or may be combined with one or more than one additional active pharmaceutical ingredients.

II. Method for Synthesis (a) Method for Producing a Compound Comprising Formula (I)

In another embodiment, the disclosure provides a method of making the compound comprising Formula (I). The method comprises contacting a compound comprising Formula (III) with a phenylacetonitrile or a benzyl triphenyl phosphine bromide in the presence of a proton acceptor. The compound of Formula (II) comprises:

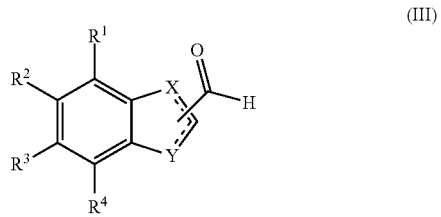

(III)

wherein, $R^1$, $R^2$, $R^3$, $R^4$, X, and Y may be chosen as described in section (I).

The compound comprising Formula (III) is an aldehyde. As indicated by the figure, the aldehyde may be connected at any of the non-fused positions of the five-membered ring including through a bond to X, through a bond to Y, or through a bond to the carbon atom between X and Y.

$R^1$, $R^2$, $R^3$, $R^4$, X and Y may be chosen as described in section (I). In some embodiments, the compound comprising Formula (III) is chosen from benzo[b]thiophene-2-carbaldehydes, benzo[b]thiophene-3-carbaldehydes, benzofuran-2-carboxaldehydes, benzofuran-3-carboxaldehydes, indole-2-carboxaldehydes, indole-3-carboxaldehydes, and benzthiazole-2-carboxaldehydes.

In one embodiment, the compound comprising Formula (III) is contacted with a phenylacetonitrile. Phenylacetonitriles have the following generic structure:

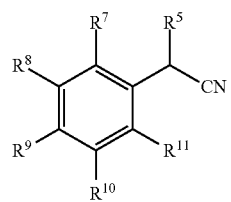

wherein, $R^5$, $R^7$, $R^8$, $R^9$, $R^{10}$, and $R^{11}$ may be chosen as described in section (I).

In preferred embodiments, the phenylacetonitrile is chosen from phenylacetonitrile, 3,4,5-trimethoxy phenyl acetonitrile, 3,4-dimethoxyphenylacetonitrile, and 4-hydroxy, 3,5-trimethoxyphenylacetonitrile.

The mole to mole ratio of the compound comprising Formula (III) to the phenyl acetonitrile can range over different embodiments of the invention. In one embodiment, the ratio of the compound comprising Formula (III) to the phenylacetonitrile varies from about 0.9:1 to about 1:10. In some embodiments, the mole to mole ratio of the compound comprising Formula (III) to the phenylacetonitrile is about 1:1 to about 1:1.5. In various embodiments, the mole to mole ratio of the compound comprising Formula (III) to the phenylacetonitrile is about 1:1, about 1:1.1, about 1:1.2, about 1:1.3, about 1:1.4, or about 1:1.5. In an exemplary embodiment, the mole to mole ratio of the compound comprising Formula (III) to the phenylacetonitrile is 1:1.

In another embodiment, the compound comprising Formula (III) is contacted with a benzyl triphenyl phosphine. A benzyl triphenyl phosphine generally comprises the following structure:

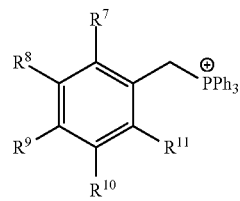

wherein, $R^7$, $R^8$, $R^9$, $R^{10}$, and $R^{11}$ may be chosen as described in section (I). An acceptable counterion is generally present. In preferred embodiments, the counterion is bromide.

In particular embodiments, benzyl triphenyl phosphines may include 3,4,5 trimethoxybenzyl triphenyl phosphine bromide, 3,4-dimethoxybenzyl triphenyl phosphine bromide, 4-hydroxy, and 3,5-dimethoxybenzyl triphenyl phosphine bromide.

The mole to mole ratio of the compound comprising Formula (III) to the benzyl triphenyl phosphine can range over different embodiments of the invention. In one embodiment, the ratio of the compound comprising Formula (III) to the benzyl triphenyl phosphine varies from about 0.9:1 to about 1:10. In some embodiments, the mole to mole ratio of the compound comprising Formula (III) to the benzyl triphenyl phosphine is about 1:1 to about 1:1.5. In various embodiments, the mole to mole ratio of the compound comprising Formula (III) to the benzyl triphenyl phosphine is about 1:1, about 1:1.1, about 1:1.2, about 1:1.3, about 1:1.4, or about 1:1.5. In an exemplary embodiment, the mole to mole ratio of the compound comprising Formula (III) to the benzyl triphenyl phosphine is 1:1.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In exemplary embodiments, the solvent is an alcohol solvent. In one preferred embodiment, the solvent is methanol.

A proton acceptor is generally added to facilitate the reaction. The proton acceptor generally has a pKa greater than about 7, or from about 7 to about 13, or more preferably from about 8 to about 10. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In one preferred embodiment, the proton acceptor is sodium methoxide.

The amount of the proton acceptor which is added may vary. Generally, the proton acceptor is added in excess to the compound comprising Formula (III). In some embodiments, the mole to mole ratio of the compound comprising Formula (III) to the proton acceptor can range from about 1:1.1 to about 1:100. In some embodiments, the mole to mole ratio of the compound comprising Formula (III) to the proton acceptor is about 1:10, about 1:20, about 1:30, about 1:40, about 1:50, about 1:60, about 1:70, about 1:80, or about 1:100. In still other embodiments, the mole to mole ratio of the compound comprising Formula (III) to the proton acceptor is about 1:41, about 1:42, about 1:43, about 1:44, about 1:45, about 1:46, about 1:47, about 1:48, or about 1:49. In one preferred embodiment, the mole to mole ratio of the compound comprising Formula (III) to the proton acceptor is 1:47.

The amount of time over which the reaction is conducted may also vary within different embodiments. In some embodiments, the reaction may be conducted over a period of 2 hours to 8 hours. In particular embodiments, the reaction is carried out for about 2 hours, about 3 hours, about 4 hours, about 5 hours, about 6 hours, about 7 hours, or about 8 hours. In preferred embodiments, the reaction is conducted for about 4 hours.

The temperature may vary over different embodiments, in some embodiments the temperature may range from about 20° C. to about 80° C. In particular embodiments the temperature may range from about 20° C. to about 30° C., from about 30° C. to about 40° C., from about 40° C. to about 50° C. from about 50° C. to about 60° C., from about 60° C. to about 70° C., or from about 70° C. to about 80° C.

In some embodiments, a further isomerization step is required to convert between (E) and (Z) isomers. This step may be accomplished by methods known in the art. In one preferred embodiment, the isomers are transformed by stirring the compounds under a UV light for 12 to 72 hours.

The synthesized compounds may be used in their crude form or they may be purified. The compounds may be purified by any suitable method known in the art including through column chromatography, crystallization, distillation, extraction, and the like. In one preferred embodiment, the compounds are recrystallized from a solvent.

III. Methods of Use for the Compound Comprising Formula (I)

In still another aspect, the present disclosure provides a method of inhibiting tubulin polymerization in a subject. The method comprises administering a compound comprising Formula (I) to a subject.

Without being bound to any theory, compounds comprising Formula (I) are thought to bind to tubulin. The binding at this site is thought to inhibit tubulin polymerization, and in turn, inhibit formation of vasculature. In tumors, a developing vasculature is critical to tumor growth and migration. Accordingly, inhibition of tubulin polymerization is important to the treatment of various disease states.

In another embodiment, a method for treating cancer is provided. The method comprises administering a compound comprising Formula (I) to a subject. Cancers treatable by the method may include, without limitation, prostate cancer, ovarian cancer, breast cancer, brain cancer, hepatic cancer, leukemia, lung cancer, colon cancer, CNS cancer, melanoma, renal cancer, pancreatic cancer, gastric cancer, lymphoma and the like.

The compounds may be administered to the subject by a variety of routes. For example, a compound comprising Formula (I) may be administered orally via a solid or liquid dosage form (tablet, gel cap, time release capsule powder, solution, or suspension in aqueous or non-aqueous liquid), parenterally (i.e., subcutaneously, intradermally, intravenously, (i.e., as a solution, suspension or emulsion in a carrier), intramuscularly, intracranially, or intraperitoneally), or topically (i.e., transdermally or transmucosally, including, but not limited to buccal, rectal, vaginal and sublingual). In one embodiment, the compounds may be administered in saline or with a pharmaceutically acceptable excipient as described in section (I). The compound may be administered as primary therapy, or as adjunct therapy, either following local intervention (surgery, radiation, local chemotherapy) or in conjunction with at least one other chemotherapeutic agent.

Suitable subjects may include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. The subject can be of any age without limitation. In a preferred embodiment, the subject may be a human.

Generally, the compound comprising Formula (I) will be administered in a therapeutically effective amount which includes prophylactic amounts or lower dosages for example, when combined with another agent. As used herein, "an effective amount" refers to doses of compound sufficient to provide circulating concentrations high enough to impart a beneficial effect on the recipient thereof. The amount to be administered depends on the lipophilicity of the specific compound selected, since it is expected that this property of compounds will cause it to partition into fat deposits of the subject. The precise amount to be administered can be determined by the skilled practitioner in view of desired dosages, side effects, and medical history of the patient.

The compounds comprising Formula (I) may also be characterized by their cytotoxic effects when contacted with cells. In some embodiments, the compounds inhibit the growth of a cell. In other embodiments, the compounds kill cells. Accordingly, the compounds of the present invention may be characterized by $GI_{50}$ values and $LC_{50}$ values. $GI_{50}$ refers to the molar drug concentration required to cause 50% growth inhibition compared to an untreated cell. $LC_{50}$ refers to the concentration required to kill 50% of cells. In still another embodiment, the disclosure provides a method for inhibiting growth of a cell by contacting the cells with a compound comprising Formula (I), and in a still further embodiment, the disclosure provides a method for killing cells by contacting the cells with a compound comprising Formula (I). Cells may be chosen from, without limitation, those listed in TABLE 1.

In some embodiments, the compounds comprising Formula (I) have an $LC_{50}$ of less than about 100 μM, or less than 80 μM, or less than about 60 μM, or less than about 40 μM, or less than about 20 μM, or less than about 1 μM. In other embodiments, the compounds comprising Formula (I) have a $GI_{50}$ of less than about 100 μM, or less than 80 μM, or less than about 60 μM, or less than about 40 μM, or less than about 20 μM, or less than about 1 μM.

IV. Compositions of the Compound Comprising Formula (II)

(a) Compound Comprising Formula (II)

One aspect of the invention provides compounds comprising Formula (II):

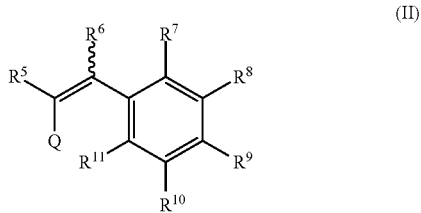

wherein:
  $R^7$, $R^8$, $R^9$, $R^{10}$, $R^{11}$ are independently chosen from hydrogen, hydrocarbyl, substituted hydrocarbyl, alkoxy, alkylalkylamino, amidine, amino, carboxyl, cyano, ester, halogen, hydroxyl, and nitro;
  $R^5$ and $R^6$ are independently chosen from hydrogen, hydrocarbyl, substituted hydrocarbyl, carboxyl, ester, and cyano; and
  Q is a quinolinyl moiety,
    with the proviso that when $R^6$ is cyano, $R^8$ and $R^9$ are not each $OCH_3$.

Q is a quinolinyl moiety. Quinolinyl moieties are nitrogen containing heterocyclic aromatic compounds which have the structure below. The atoms of the quinolinyl moiety are numbered as shown in the figure. The quinolinyl moiety may be bonded to the remainder of the compound comprising Formula (II) via any of the numbered positions below. In some embodiments, Q is a 1-quinolinyl, a 2-quinolinyl, a 3-quinolinyl, a 4-quinolinyl, a 5-quinolinyl, a 6-quinolinyl, a 7-quinolinyl, or an 8-quinolinyl. In preferred embodiments, Q is a 2-quinolinyl or 3-quinolinyl.

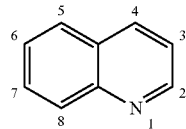

The quinolinyl may be further substituted. Further substitutions may be independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. Amidine nitrogen groups may be further substituted by hydrogen, hydrocarbyl, or substituted hydrocarbyl at each position. Preferably, the amidine nitrogens are each substituted by hydrogen. Where the substitution is an amine, the amine may be a primary, secondary, or tertiary amine. Preferably, amine substituents are lower alkyl groups. Ester groups may be attached to the quinolinyl at either the carbonyl end or at the oxygen end of the ester. The opposite terminus may be hydrocarbyl or substituted hydrocarbyl, and is preferably a lower alkyl.

$R^7$, $R^8$, $R^9$, $R^{10}$, and $R^{11}$ in the compound comprising Formula (I) are independently chosen from hydrogen, hydrocarbyl, substituted hydrocarbyl, alkylalkylamino, amidine, amino, carboxyl, cyano, ester, halogen, hydroxyl, and nitro. Alkylalkylamino groups are disubstituted amine groups. Each of the alkyl groups may be the same or different. In one embodiment, both alkyl groups are lower alkyl groups. The amidine nitrogen groups may be further substituted by hydrogen, hydrocarbyl, or substituted hydrocarbyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached at either the carbonyl end or at the oxygen end of the ester. The opposite terminus of the ester may be hydrocarbyl or substituted hydrocarbyl. Preferably, the ester is a lower alkyl.

In certain embodiments, $R^7$, $R^8$, $R^9$, $R^{10}$, and $R^{11}$ are independently chosen from hydrogen, hydroxyl, and alkoxy, with the proviso that when $R^8$ and $R^9$ are $OCH_3$, then $R^{10}$ is not hydrogen, and when $R^9$ and $R^{10}$ are $OCH_3$, then $R_8$ is not hydrogen. In another embodiment, $R^7$, $R^8$, $R^9$, $R^{10}$, and $R^{11}$ are independently chosen from hydrogen and hydroxyl. In one preferred embodiment, $R^7$ and $R^{11}$ are hydrogen. In another embodiment, $R^8$, $R^9$, and $R^{10}$ are independently chosen from hydrogen, methoxy, ethoxy, benzyloxy, substituted benzyloxy, hydroxyl, and lower alkyl groups. In one embodiment, $R^8$, $R^9$, and $R^{10}$ are independently chosen from hydrogen and hydroxyl. In one preferred embodiment, $R^8$, $R^9$, and $R^{10}$ are each hydroxy, and in still another preferred embodiment, $R^8$ and $R^{10}$ are hydroxy, and $R^9$ is hydrogen.

Various substitution patterns on the phenyl ring are within the scope of the present invention. In one embodiment, where $R^8$ and $R^9$ are substituted with other than hydrogen, then $R^{10}$ is not hydrogen. In yet another embodiment, where $R^9$ and $R^{10}$ are substituted with other than hydrogen then $R^8$ is not hydrogen. In preferred embodiments, $R^8$, $R^9$, and $R^{10}$ are each substituted with other than hydrogen. In still other preferred embodiments, $R^8$ and $R^{10}$ are substituted with other than hydrogen, and $R^9$ is substituted with hydrogen.

$R^5$ and $R^6$ are independently chosen from hydrogen, hydrocarbyl, substituted hydrocarbyl, carboxyl, ester, and cyano. Ester groups may be attached at either the carbonyl end or at the oxygen end of the ester. The terminus of the ester that is not bound to the double bond may be hydrocarbyl or substituted hydrocarbyl. Preferably, the ester is a lower alkyl ester.

In one embodiment, $R^5$ is hydrogen and $R^6$ is chosen from hydrogen, cyano, and carboxyl. In still another embodiment, $R^5$ is hydrogen and $R^6$ is cyano. In yet another embodiment, $R^5$ and $R^6$ are hydrogen. In one embodiment, where $R^6$ is cyano, $R^8$ and $R^9$ are not each $OCH_3$. In another embodiment, where $R^6$ is cyano, $R^9$ and and $R^{10}$ are not each methoxy.

The wavy bond at $R^6$ indicates that $R^6$ may be at either geometric position on the double bond. Accordingly, the double bond may be (E) or (Z), which are defined according to the IUPAC convention. In one embodiment, the double bond may have an (E) configuration, and in another embodiment, the double bond may have a (Z) configuration.

The compound comprising Formula (II) may be a free form or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents.

In one embodiment, the disclosure provides a compound comprising Formula (II)(a):

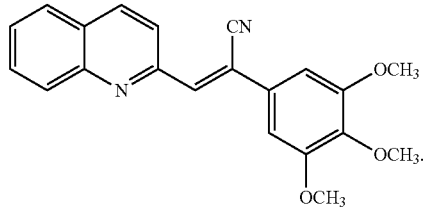

In still another embodiment, the disclosure provides a compound comprising Formula (I)(b):

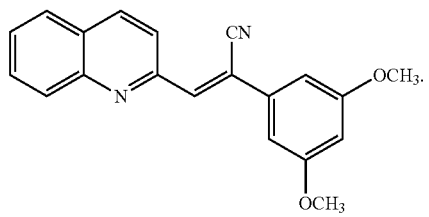

In still another embodiment, the disclosure provides a compound comprising Formula (II)(c):

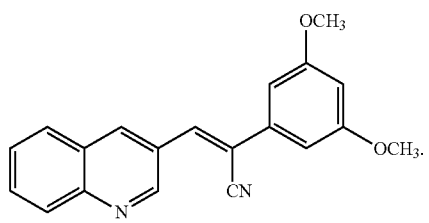

In still a further embodiment, the disclosure provides a compound comprising Formula (II)(d):

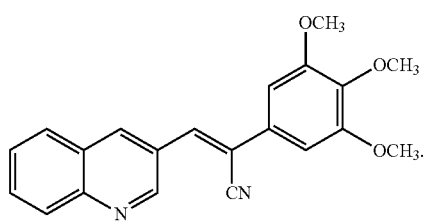

Figure 4A:
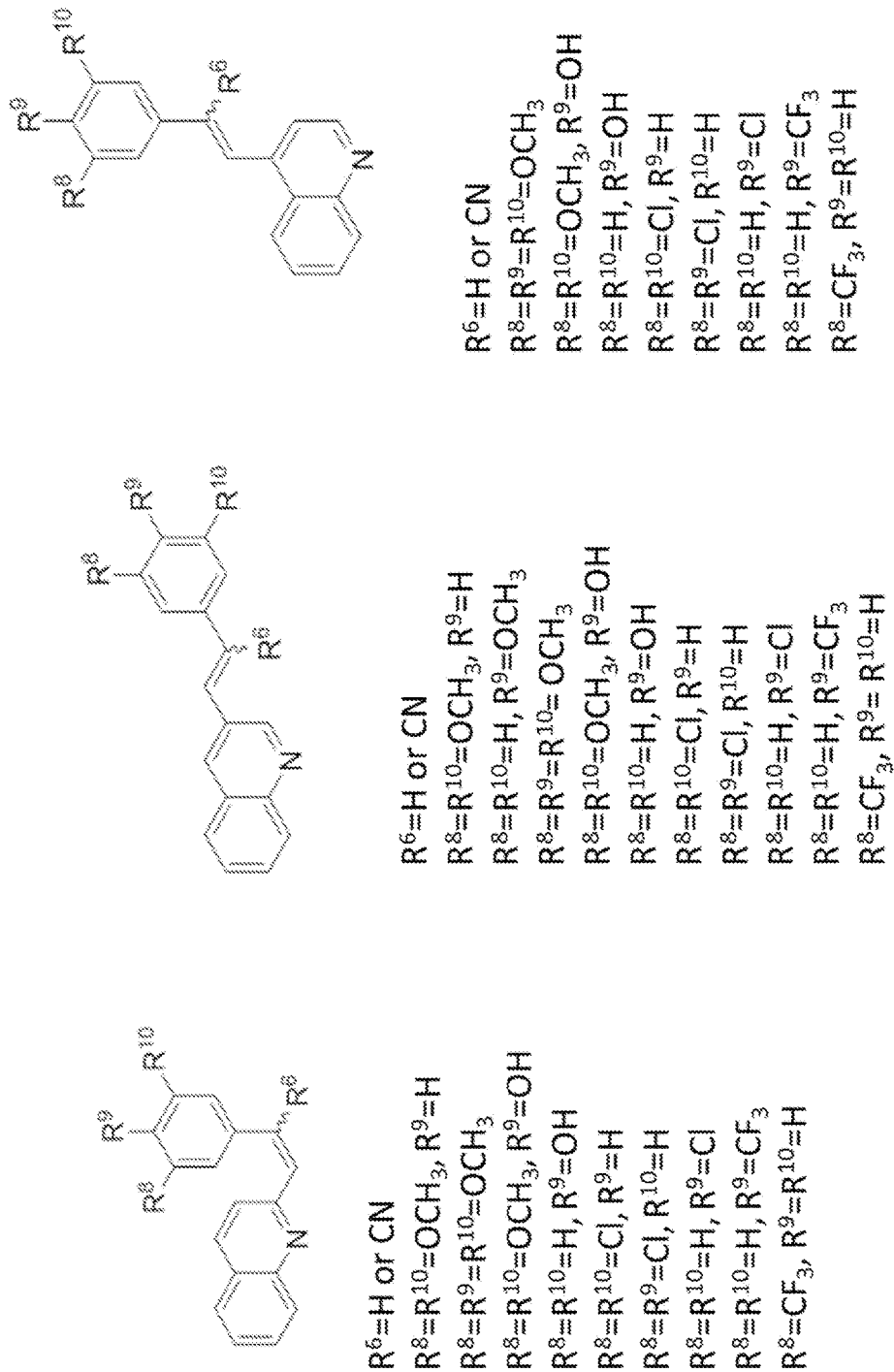
FIG. 4A, FIG. 4B and FIG. 4C show exemplary compounds comprising Formula (II).
Figure 4B:
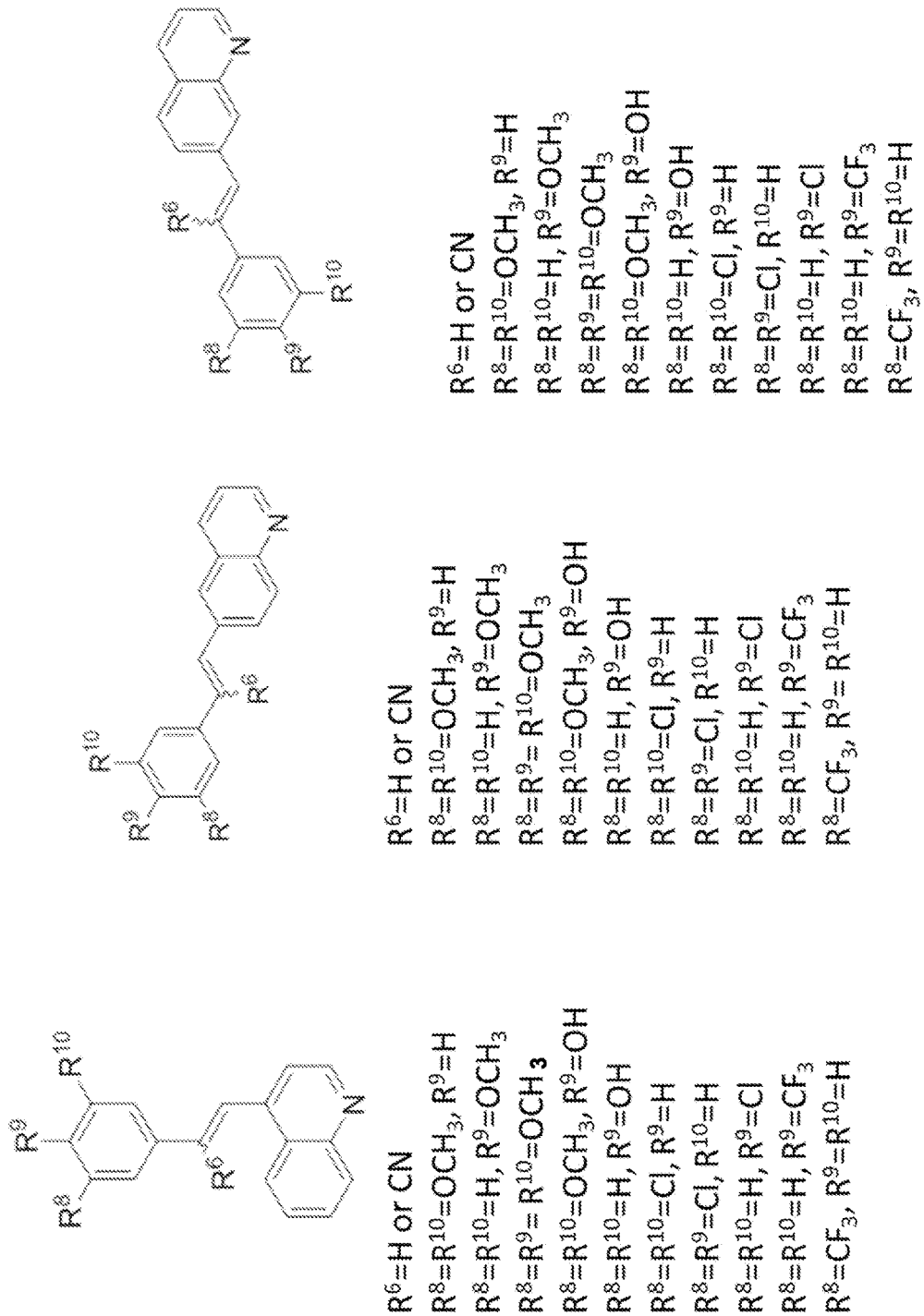
Figure 4C:
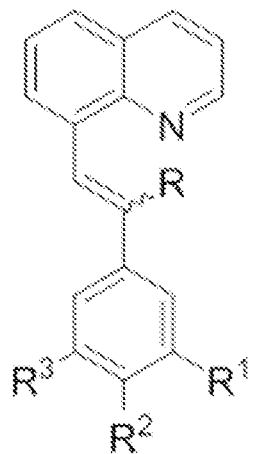

Additional embodiments are shown in FIGS. 4(A)-(C).

(b) Pharmaceutical Compositions

The disclosure also provides a pharmaceutical composition comprising the compound comprising Formula (II) and at least one pharmaceutically acceptable excipient. In various embodiments, one or more of the compounds described in section (I) may be combined with at least one pharmaceutically acceptable excipient.

(i) Excipient

A pharmaceutical composition of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Buffers may include phosphates, carbonates, citrates, and the like. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate, or EDTA (ethylenediaminetetraacetic acid), EGTA (ethylene glycol tetraacetic acid), BHA (butylated hydroxyanisole), BHT (butylated hydroxytoluene), and the like.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants may include minerals such as talc or silica; and fats such as vegetable stearin, magnesium stearate, or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid, or cream dosage form. Methods of formulating a solid, liquid, or cream dosage form are known in the art.

(ii) Optional Additional Pharmaceutical Ingredient

Optionally, the compound comprising Formula (I) may be combined with other compounds comprising Formula (I) or may be combined with one or more than one additional active pharmaceutical ingredients.

V. Method for Producing a Compound Comprising Formula (II)

In another embodiment, the disclosure provides a method of making the compound comprising Formula (II). The method comprises contacting a quinolinyl carboxaldehyde with a phenylacetonitrile or a benzyl triphenyl phosphine bromide in the presence of a proton acceptor. A quinolinyl carboxaldehyde is a quinolinyl moiety, as described in Section (IV), which is substituted with an aldehyde moiety at one or more of the positions 1-8. Further substitution on the quinolinyl moiety may be as described in Section (II). In preferred embodiments, the quinolinyl carboxaldehyde is quinoline-2-carboxaldehyde, quinoline-3-carboxaldehyde, quinoline-4-carboxaldehyde, quinoline-5-carboxaldehyde, quinoline-6-carboxaldehyde.

The carboxaldehyde is contacted with phenylacetonitrile. Phenylacetonitriles have the following generic structure:

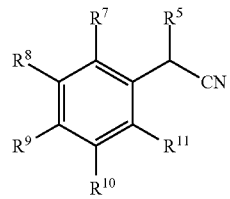

wherein, $R^5$, $R^7$, $R^8$, $R^9$, $R^{10}$, and $R^{11}$ may be chosen as described in section (I).

In preferred embodiments, the phenylacetonitrile is chosen from phenylacetonitrile, 3,4,5-trimethoxy phenyl acetonitrile, 3,4-dimethoxyphenylacetonitrile, and 4-hydroxy, 3,5-trimethoxyphenylacetonitrile.

The mole to mole ratio of the carboxaldehyde to the phenyl acetonitrile can range over different embodiments of the invention. In one embodiment, the ratio of the carboxaldehyde to the phenylacetonitrile varies from about 0.9:1 to about 1:10. In some embodiments, the mole to mole ratio of the carboxaldehyde to the phenylacetonitrile is about 1:1 to about 1:1.5. In various embodiments, the mole to mole ratio of the carboxaldehyde to the phenylacetonitrile is about 1:1, about 1:1.1, about 1:1.2, about 1:1.3, about 1:1.4, or about 1:1.5. In an exemplary embodiment, the mole to mole ratio of the carboxaldehyde to the phenylacetonitrile is 1:1.

In another embodiment, the compound comprising Formula (II) is contacted with a phenyl triphenyl phosphine. A phenyl triphenyl phosphine generally comprises the following structure:

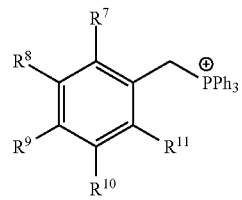

wherein, $R^7$, $R^8$, $R^9$, $R^{10}$, and $R^{11}$ may be chosen as described in section (I).

An acceptable counter ion is generally present. In preferred embodiments, the counter ion is bromide.

In particular embodiments, phenyl triphenyl phosphines may include 3,4,5 trimethoxyphenyl triphenyl phosphine bromide, 3,4-dimethoxyphenyl triphenyl phosphine bromide, 4-hydroxy, and 3,5-dimethoxyphenyl triphenyl phosphine bromide.

The mole to mole ratio of the carboxaldehyde to the phenyl triphenyl phosphine can range over different embodiments of the invention. In one embodiment, the ratio of the carboxaldehyde to the phenyl triphenyl phosphine varies from about 0.9:1 to about 1:10. In some embodiments, the mole to mole ratio of the carboxaldehyde to the phenyl triphenyl phosphine is about 1:1 to about 1:1.5. In various embodiments, the mole to mole ratio of the carboxaldehyde to the phenyl triphenyl phosphine is about 1:1, about 1:1.1, about 1:1.2, about 1:1.3, about 1:1.4, or about 1:1.5. In an exemplary embodiment, the mole to mole ratio of the carboxaldehyde to the phenyl triphenyl phosphine is 1:1.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In exemplary embodiments, the solvent is an alcohol solvent. In one preferred embodiment, the solvent is methanol.

A proton acceptor is generally added to facilitate the reaction. The proton acceptor generally has a pKa greater than about 7, or from about 7 to about 13, or more preferably from about 8 to about 10. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In one preferred embodiment, the proton acceptor is sodium methoxide.

The amount of the proton acceptor which is added may vary. In some embodiments, the mole to mole ratio of the carboxaldehyde to the proton acceptor can range from about 1:1 to about 1:10. In some embodiments, the mole to mole ratio of the carboxaldehyde to the proton acceptor is about 1:1, about 1:2, about 1:3, about 1:4, about 1:5, about 1:6, about 1:7, about 1:8, or about 1:10. In still other embodiments, the mole to mole ratio of the carboxaldehyde to the proton acceptor is about 1:1.2, about 1:1.3, about 1:1.4, about 1:1.5, about 1:1.6, about 1:1.7, about 1:1.8, or about 1:9. In one preferred embodiment, the mole to mole ratio of the carboxaldehyde to the proton acceptor is about 1:2.

The amount of time over which the reaction is conducted may also vary within different embodiments. In some embodiments, the reaction may be conducted over a period of 2 hours to 8 hours. In particular embodiments, the reaction is carried out for about 2 hours, about 3 hours, about 4 hours, about 5 hours, about 6 hours, about 7 hours, or about 8 hours. In preferred embodiments, the reaction is conducted for about 4 hours.

The temperature may vary over different embodiments, in some embodiments the temperature may range from about 20° C. to about 80° C. In particular embodiments the temperature may range from about 20° C. to about 30° C., from about 30° C. to about 40° C., from about 40° C. to about 50° C. from about 50° C. to about 60° C., from about 60° C. to about 70° C., or from about 70° C. to about 80° C.

The synthesized compounds may be used in their crude form or they may be purified. The compounds may be purified by any suitable method known in the art including through column chromatography, crystallization, distillation, extraction, and the like. In one preferred embodiment, the compounds are recrystallized from a solvent.

VI. Methods of Use for the Compound Comprising Formula (II)

In still another aspect, the present disclosure provides a method of inhibiting tubulin polymerization in a subject. The method comprises administering a compound comprising Formula (II) to a subject.

Without being bound to any theory, compounds comprising Formula (II) are thought to bind to tubulin. The binding at this site is thought to inhibit tubulin polymerization, and in turn, inhibit formation of vasculature. In tumors, a developing vasculature is critical to tumor growth and migration. Accordingly, inhibition of tubulin polymerization is important to the treatment of various disease states.

In another embodiment, a method for treating cancer is provided. The method comprises administering a compound comprising Formula (II) to a subject. Cancers treatable by the method may include, without limitation, prostate cancer, ovarian cancer, breast cancer, brain cancer, hepatic cancer, leukemia, lung cancer, colon cancer, CNS cancer, melanoma, renal cancer, pancreatic cancer, gastric cancer, lymphoma and the like.

The compounds may be administered to the subject by a variety of routes. For example, a compound comprising Formula (II) may be administered orally via a solid or liquid dosage form (tablet, gel cap, time release capsule powder, solution, or suspension in aqueous or non-aqueous liquid), parenterally (i.e., subcutaneously, intradermally, intravenously, (i.e., as a solution, suspension or emulsion in a carrier), intramuscularly, intracranially, or intraperitoneally), or topically (i.e., transdermally or transmucosally, including, but not limited to buccal, rectal, vaginal and sublingual). In one embodiment, the compounds may be administered in saline or with a pharmaceutically acceptable excipient as described in section (IV). The compound may be administered as primary therapy, or as adjunct therapy, either following local intervention (surgery, radiation, local chemotherapy) or in conjunction with at least one other chemotherapeutic agent.

Suitable subjects may include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. The subject can be of any age without limitation. In a preferred embodiment, the subject may be a human.

Generally, the compound comprising Formula (II) will be administered in a therapeutically effective amount which includes prophylactic amounts or lower dosages for example, when combined with another agent. As used herein, "an effective amount" refers to doses of compound sufficient to provide circulating concentrations high enough to impart a beneficial effect on the recipient thereof. The precise amount to be administered can be determined by the skilled practitioner in view of desired dosages, side effects, and medical history of the patient.

The compounds comprising Formula (II) may also be characterized by their cytotoxic effects when contacted with cells. In some embodiments, the compounds inhibit the growth of a cell. In other embodiments, the compounds kill cells. Accordingly, the compounds of the present invention may be characterized by $GI_{50}$ values and $LC_{50}$ values. $GI_{50}$ refers to the molar drug concentration required to cause 50% growth inhibition compared to an untreated cell. $LC_{50}$ refers to the concentration required to kill 50% of cells. In still another embodiment, the disclosure provides a method for inhibiting growth of a cell by contacting the cells with a compound comprising Formula (II), and in a still further embodiment, the disclosure provides a method for killing cells by contacting the cells with a compound comprising Formula (II). Cells may be chosen from, without limitation, those listed in TABLE 2.

In some embodiments, the compounds comprising Formula (I) have an $LC_{50}$ of less than about 100 µM, or less than 80 µM, or less than about 60 µM, or less than about 40 µM, or less than about 20 µM, or less than about 1 µM. In other embodiments, the compounds comprising Formula (II) have a $GI_{50}$ of less than about 100 µM, or less than 80 µM, or less than about 60 µM, or less than about 40 µM, or less than about 20 µM, or less than about 1 µM.

VII. Compositions of the Compound Comprising Formula (V)

(a) Compound Comprising Formula (V)

One aspect of the invention provides compounds comprising Formula (V):

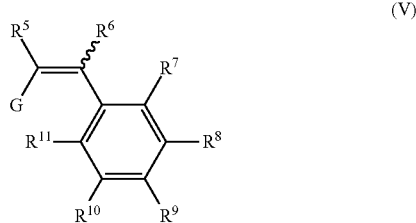

wherein:
G is chosen from

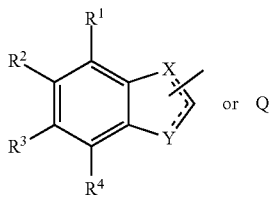

Q is a quinolinyl moiety;
$R^1$, $R^2$, $R^3$, $R^4$, $R^7$, $R^8$, $R^9$, $R^{10}$, $R^{11}$ are independently chosen from hydrogen, hydrocarbyl, substituted hydrocarbyl, alkylalkylamino, amidine, amino, carboxyl, cyano, ester, halogen, hydroxyl, and nitro;
$R^5$ and $R^6$ are independently chosen from hydrogen, hydrocarbyl, substituted hydrocarbyl, carboxyl, ester, and cyano;
X and Y are independently chosen from O, C, $CR^{12}$, $CR^{12}R^{13}$, S, $SR^{14}N$, or $NR^{15}$; and
$R^{12}$, $R^{13}$, $R^{14}$, and $R^{15}$ are independently chosen from hydrogen, hydrocarbyl, substituted hydrocarbyl, alkylalkylamino, amidine, amino, carboxyl, cyano, ester, halogen, hydroxyl, and nitro.

All variables are as described in Sections (I) and (IV).

The compound comprising Formula (V) may be used as a polymerase inhibitor, as described in Sections (III) and (VI). The compositions may be formulated as a pharmaceutical composition as described in Sections (I) and (IV).

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1$O—, $R^1R^2$N—, or $R^1$S—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein refers to straight or branched chain alkyl groups having in the range of about 1 to about 10 carbon atoms. A substituted alkyl group has one or more heteroatom substituents as described in the definition of substituted hydrocarbyl.

The term "alkylaryl" refers to alkyl substituted aryl groups, and "substituted alkylaryl" refers to alkylaryl groups further bearing one or more substituents.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl, or substituted naphthyl.

The term "arylalkynyl" refers to aryl-substituted alkynyl groups and "substituted arylalkynyl" refers to arylalkynyl groups further bearing one or more substituents.

The term "aroyl" refers to aryl-substituted species such as benzoyl and "substituted aroyl" refers to aroyl moieties further bearing one or more substituents as set forth above.

The term "cycloalkyl" refers to cyclic ring-containing moieties containing in the range of about 3 up to 7 carbon atoms and "substituted cycloalkyl" refers to cycloalkyl moieties further bearing one or more substituents.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and having in the range of 2 up to 12 carbon atoms, or preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbamate, carbocyclo, cyano, ester, ether, halogen, heterocyclo, hydroxyl, keto, ketal, phospho, nitro, thio, trifluoromethyl, sulfonyl, sulfonamide, and the like.

EXAMPLES

Example 1

Synthesis of (E)-3-(benzo[b]thiophen-2-yl)-2-(3,4,5-trimethoxyphenyl)acrylonitrile A mixture of benzo[b]thiophene-2-carbaldehyde (1.62 g; 0.01 mol) and 2-(3,4,5-trimethoxyphenyl)acetonitrile (2.07 g; 0.01 mol), sodium methoxide (2.5 gm) in methanol (50 ml) were stirred at reflux temperature for 3 hours. The reaction mass was cooled to room temperature, and crushed ice was added to get solid product. The crude solid was separated by filtration and washed several times with cold methanol (3×5 ml). The isolated yellow solid recrystallized from methanol gave (Z)-3-(benzo[b]thiophen-2-yl)-2-(3,4,5-trimethoxyphenyl)acrylonitrile as a yellow crystalline product.

The compound (Z)-3-(benzo[b]thiophen-2-yl)-2-(3,4,5-trimethoxy-phenyl)acrylonitrile was dissolved in methanol under reflux conditions and stirred for 48 hours under the UV light. The colorless solution was cooled to room temperature, and allowed to crystallize from methanol as white crystalline product, (E)-3-(benzo[b]thiophen-2-yl)-2-(3,4,5-trimethoxyphenyl)acrylonitrile, MF: $C_{20}H_{17}NO_3S$, mp: 201-203° C., $^1$H NMR (DMSO-$d_6$): 3.76 (s, 3H), 3.78 (s, 6H), 6.81 (s, 2H), 7.36-7.37 (t, 2H), 7.85-7.89 (m, 3H), 8.05 (s, 1H) ppm; $^{13}$C NMR (DMSO-$d_6$): 56.45, 61.32, 106.53, 112.34, 120.10, 122.42, 124.65, 125.13, 126.85, 127.01, 131.71, 136.93, 137.94, 138.10, 139.64, 141.94, 154.15 ppm.

Example 2

Synthesis of (Z)-2-(3,5-dimethoxyphenyl)-3-(1H-indol-3-yl)acrylonitrile

A mixture of 1 H-indole-3-carbaldehyde (1.45 g; 0.01 mol) and 2-(3,5-dimethoxyphenylacetonitrile (1.77 g; 0.01 mol), sodium methoxide (2.5 gm) in methanol (50 ml) were stirred at reflux temperature for 4 hrs. The reaction mass was cooled to room temperature, and crushed ice was added to get solid product, the crude solid was separated by filtration and washed several times with cold methanol (3×5 ml). The isolated yellow solid recrystallized from methanol gave (Z)-2-(3,5-dimethoxyphenyl)-3-(1H-indol-3-yl)acrylonitrile as a yellow crystalline product; MF: $C_{19}H_{16}N_2O_2$, mp: 170-172° C., $^1$H NMR (CDCl$_3$): δ3.86 (s, 6H), 6.45 (s, 1H), 6.82 (s, 2H), 7.25-7.29 (m, 2H), 7.44-7.46 (d, J=8 Hz, 1H), 7.75-7.77 (d, J=7.2 Hz, 1H), 7.87 (s, 1H); 8.44 (s, 1H), 8.83 (brs, 1H, NH) ppm; $^{13}$C NMR (CDCl$_3$): 55.52, 100.10, 103.67, 111.79, 118.00, 119.95, 121.38, 123.50, 126.40, 127.28, 133.78, 135.45, 136.84, 161.21 ppm.

Example 3

Synthesis of (E)-2-(3,4,5-trimethoxystyryl)benzofuran

A mixture of benzofuran-2-carbaldehyde (0.146 g; 0.001 mol) and triphenyl(3,4,5-trimethoxybenzyl)phosphonium bromide (0.523 g; 0.001 mol), sodium methoxide (2.5 gm) in methanol (50 ml) were stirred at room temperature for 4 hours. Crushed ice was added to get solid product, and the crude solid was separated by filtration and washed several times with cold methanol (3×5 ml). The isolated pale yellow solid recrystallized from methanol gave (E)-2-(3,4,5-tri methoxystyryl)benzofuran as a pale yellow crystalline product; MF: $C_{19}H_{18}O_4$, mp: 124-126 ° C., $^1$H NMR (CDCl$_3$): δ 3.87 (s, 3H), 3.91 (s, 6H), 6.66 (s, 1H), 6.75 (s, 2H), 6.88-6.92 (d, J=16Hz, 1H), 7.20-7.26 (m, 3H), 7.44-7.46 (d, J=8.4 Hz, 1H), 7.51-7.53 (d, J=7.6Hz, 1H) ppm; $^{13}$C NMR (CDCl$_3$): 56.11, 60.98, 103.72, 105.04, 110.82, 115.88, 120.79, 122.90, 124.60, 129.11, 130.21, 132.25, 138.36, 153.44, 154.83, 154.94 ppm.

Example 4

Synthesis of (E)-2-(3,4,5-trimethoxystyryl)benzo[d]thiazole

A mixture of benzo[d]thiazole-2-carbaldehyde (0.163 g; 0.001 mol) and triphenyl(3,4,5-trimethoxybenzyl)phosphonium bromide (0.523 g; 0.001 mol), sodium methoxide (2.5 gm) in methanol (50 ml) were stirred at room temperature for 4 hours. Crushed ice was added to get a solid product, and the crude solid was separated by filtration and washed several times with cold methanol (3×5 ml). The isolated pale yellow solid recrystallized from methanol gave (E)-2-(3,4,5-trimethoxystyryl)benzo[d]thiazole as a pale yellow crystalline product; MF: $C_{18}H_{17}NO_3S$, mp: 125-127° C., $^1$HNMR (CDCl$_3$): δ 3.91 (s, 3H), 3.93 (s, 6H), 6.83 (s, 2H), 7.33-7.48 (m, 4H), 7.87 (s, 1H), 8.0 (s, 1H) ppm; $^{13}$C NMR (CDCl$_3$): δ 56.12, 60.96, 104.47, 121.48, 122.89, 125.32, 126.33, 130.95, 134.26, 137.47, 153.5, 153.8, 166.78 ppm.

Example 5

In Vitro Growth Inhibition and Cytotoxicity Formula (I)

In a primary screen, all synthesized compounds were evaluated for their cytotoxic potency at the National Cancer Institute (NCI). The compounds were considered to be active if they reduced the growth of any of the cancer cell lines to 60% or more in at least eight of the cell lines screened. They were then passed on for evaluation in a full panel of 60 different cancer cell lines. From the preliminary 60 cell screen the compounds which showed ≥60% growth inhibition in at least eight of the cancer cell lines screened were selected for further five dose studies. From all these compounds the three most active compounds were subsequently evaluated in five dose-response studies for their in vitro cytotoxic effects on growth parameters against each of the 60 human tumor cell lines. These three analogues exhibited good growth inhibition even at nanomolar levels in five dose screening against all the cancer cell lines. Cytotoxic effects of each compound were determined as $GI_{50}$ and $LC_{50}$ values, which represent the molar drug concentration required to cause 50% growth inhibition, and the concentration that kills 50% of the cells, respectively. The results are presented in TABLE 1.

TABLE 1

Growth Inhibition and Cytotoxicity Studies N-benzoyl indole analogs (Formula (I))

| Panel/cell Line | Formula (I)(a) | | Formula (I)(b) | | Formula (I)(c) | | Formula (I)(d) | |
|---|---|---|---|---|---|---|---|---|
| | $GI_{50}$ (nM) | $LC_{50}$ (μM) | $GI_{50}$ (nM) | $LC_{50}$ (μM) | $GI_{50}$ (nM) | $LC_{50}$ (μM) | $GI_{50}$ (nM) | $LC_{50}$ (μM) |
| Leukemia | | | | | | | | |
| CCEF-CEM | <10.0 | >100 | 42.4 | >100 | 0.42 | >100 | 0.13 | >100 |
| HL-60(TM) | <10.0 | >100 | 31.2 | >100 | 0.35 | >100 | 0.037 | >100 |
| K-562 | <10.0 | >100 | 43.2 | >100 | 0..26 | >100 | 0.041 | >100 |
| MOLT-4 | <10.0 | >100 | 49.1 | >100 | 0.85 | >100 | 1.28 | >100 |
| RPMI-8226 | <10.0 | >100 | 65.5 | >100 | 0.70 | >100 | 0.15 | >100 |
| SR | <10.0 | >100 | 33.4 | >100 | 0.09 | >100 | 0.036 | >100 |
| Lung Cancer | | | | | | | | |
| A549/ATCC | <10.0 | >100 | 61.8 | >100 | 0.61 | >100 | 0.11 | >100 |
| HOP-62 | <10.0 | >100 | >100 | >100 | 0.77 | >100 | 0.39 | 81.5 |
| HOP-92 | <10.0 | >100 | 68.4 | >100 | 0.17 | >100 | 0.036 | 77.4 |
| NCI-H226 | 17.9 | >100 | >100 | >100 | 1.1 | >100 | 0.24 | 88.5 |
| NCI-H23 | <10.0 | >100 | >100 | >100 | 3.09 | >100 | 0.72 | >100 |
| NCI-H322M | 18.3 | >100 | na | >100 | 15.9 | >100 | na | >100 |
| NCI-H460 | <10.0 | >100 | 39.2 | >100 | 0.41 | >100 | 0.11 | >100 |
| NCIH522 | Na | na | 27.1 | >100 | 0.43 | >100 | 0.16 | 47.9 |
| Colon Cancer | | | | | | | | |
| COLO 205 | <10.0 | 0.25 | 47.7 | 15.2 | 0.40 | 19.5 | 0.049 | 24.6 |
| HCC-2998 | 19.2 | >100 | >100 | >100 | 3.34 | >100 | 2.23 | 63.5 |
| HCT-116 | <10.0 | >100 | 42.5 | >100 | 0.522 | 77.0 | 0.0072 | >100 |
| HCT-15 | <10.0 | >100 | 53.5 | >100 | 0.40 | >100 | 0.063 | >100 |
| HT29 | <10.0 | >100 | 38.4 | >100 | 0.37 | >100 | 0.038 | >100 |
| KM12 | <10.0 | >100 | 40.9 | >100 | 0.50 | >100 | 0.072 | 41.6 |
| SW-620 | <10.0 | >100 | 44.1 | >100 | 0.44 | >100 | 0.43 | >100 |
| CNS Cancer | | | | | | | | |
| SF268 | <10.0 | >100 | 78.3 | >100 | 0.86 | >100 | 0.56 | >100 |
| SF-2395 | Na | na | 45.3 | >100 | 0.35 | >100 | 0.070 | >100 |
| SF-539 | <10.0 | >100 | 52.2 | 90.2 | 0.27 | >100 | 0.076 | 56.2 |
| SNB-19 | 39.1 | >100 | 62.1 | >100 | 0.58 | >100 | 0.095 | >100 |
| SNB-75 | <10.0 | >100 | 34.8 | >100 | 0.47 | >100 | 0.16 | >100 |
| U251 | <10.0 | >100 | 45.4 | >100 | 0.66 | 81.2 | 0.88 | >100 |
| Melanoma | | | | | | | | |
| LOX IM VI | <10.0 | >100 | 78.4 | >100 | 0.89 | 60.4 | 1.9 | 67.9 |
| MALMW-3M | <10.0 | >100 | na | >100 | 0.41 | 86.3 | 0.07 | 51.6 |
| M14 | <10.0 | >100 | 42.4 | >100 | 0.47 | 88.4 | 0.063 | 48.5 |
| MDA-MB-435 | <10.0 | >100 | 20.3 | >100 | 0.078 | >100 | 0.024 | 44.6 |
| SK-MEL-2 | <10.0 | >100 | 51.2 | >100 | 0.76 | >100 | 0.064 | 64.2 |
| SK-MEL-28 | <10.0 | >100 | 81.1 | >100 | 0.83 | >100 | 0.31 | 50.5 |
| SK-MEL-5 | <10.0 | >100 | 48.6 | >100 | 0.34 | 42.0 | 0.047 | 34.0 |
| UACC-257 | <10.0 | >100 | 48.7 | >100 | 16.4 | >100 | 15.0 | >100 |
| UACC-62 | <10.0 | >100 | 49.3 | >100 | 0.50 | >100 | 0.05 | 55.9 |
| Ovarian Cancer | | | | | | | | |
| IGROVI | <10.0 | >100 | >100 | >100 | 0.80 | >100 | 0.24 | 94.2 |
| OVCAR-3 | <10.0 | >100 | 31.2 | >100 | 0.42 | 48.1 | 0.069 | >100 |
| OVCAR-4 | <10.0 | >100 | >100 | >100 | 1.15 | >100 | 1.81 | >100 |

TABLE 1-continued

Growth Inhibition and Cytotoxicity Studies N-benzoyl indole analogs (Formula (I))

| Panel/<br>cell Line | Formula (I)(a) | | Formula (I)(b) | | Formula (I)(c) | | Formula (I)(d) | |
|---|---|---|---|---|---|---|---|---|
| | $GI_{50}$ (nM) | $LC_{50}$ (μM) | $GI_{50}$ (nM) | $LC_{50}$ (μM) | $GI_{50}$ (nM) | $LC_{50}$ (μM) | $GI_{50}$ (nM) | $LC_{50}$ (μM) |
| OVCAR-5 | <10.0 | >100 | >100 | >100 | 2.94 | >100 | 0.93 | >100 |
| OVCAR-8 | <10.0 | >100 | >100 | >100 | 2.05 | >100 | 0.39 | >100 |
| NCI/ADR-RES | <10.0 | >100 | 33.3 | >100 | 0.51 | >100 | 0.10 | >100 |
| SK-OV-3 | <10.0 | >100 | >100 | >100 | 0.65 | >100 | 0.16 | >100 |
| Renal Cancer | | | | | | | | |
| 786-0 | <10.0 | >100 | 77.3 | >100 | 0.85 | 79.8 | 1.32 | >100 |
| A498 | <10.0 | >100 | 35.3 | >100 | 0.40 | 48.4 | 0.041 | 35.8 |
| ACHN | <10.0 | >100 | >100 | >100 | 0.86 | >100 | 1.22 | >100 |
| CAKL-1 | 37.8 | >100 | 35.0 | >100 | 0.58 | >100 | 0.14 | >100 |
| RXF 393 | <10.0 | >100 | 83.7 | >100 | 0.32 | >100 | 0.14 | 97.6 |
| SNI2C | <10.0 | >100 | 77.9 | >100 | 4.09 | >100 | 9.37 | >100 |
| TK-10 | <10.0 | >100 | >100 | >100 | 8.4 | >100 | 11.1 | >100 |
| UO-31 | <10.0 | >100 | >100 | >100 | 1.15 | >100 | 0.37 | >100 |
| Prostate Cancer | | | | | | | | |
| PC-3 | <10.0 | >100 | 75.5 | >100 | .52 | >100 | 0.13 | >100 |
| DU-145 | <10.0 | >100 | >100 | >100 | 1.86 | >100 | 0.27 | >100 |
| Breast Cancer | | | | | | | | |
| MCF7 | <10.0 | >100 | 41.4 | >100 | 0.37 | >100 | 0.31 | 51.5 |
| MDA-MB-231/ATCC | <10.0 | >100 | >100 | >100 | 1.17 | >100 | 0.71 | >100 |
| HS 578T | <10.0 | >100 | >100 | >100 | 0.49 | >100 | 0.17 | >100 |
| BT-549 | <10.0 | >100 | >100 | >100 | 1.09 | 79.5 | 3.7 | 58.8 |
| T-47D | <10.0 | >100 | >100 | >100 | 0.69 | >100 | 0.96 | >100 |
| MDA-MB-468 | <10.0 | >100 | >100 | >100 | 0.66 | >100 | 0.82 | >100 |

Example 6

Synthesis of (Z)-3-(quinolin-2-yl)-2-(3,4,5-trimethoxyphenyl)acrylonitrile

A mixture of quinoline-2-carboxaldehyde (1.57 g; 0.01 mol) and 2-(3,4,5-trimethoxyphenyl) acetonitrile (2.07 g; 0.01 mol), sodium methoxide (1.0 gm) in methanol (50 ml) were stirred at reflux temperature for 3 hours. The reaction mass was cooled to room temperature, and crushed ice was added to get a solid product. The crude solid was separated by filtration and washed several times with cold methanol (3×5 ml). The isolated yellow solid was recrystallized from methanol and gave (Z)-3-(quinolin-2-yl)-2-(3,4,5-trimethoxyphenyl)acrylonitrile as a yellow fluffy product. MF: $C_{21}H_{18}N_2O_3$, mp: 106-108° C., $^1$H NMR (400 MHz, CDCl$_3$): δ 3.91 (s, 3H), 3.96 (s, 6H), 7.02 (s, 2H), 7.61 (t, 1H, $J_1$=7.6 Hz, $J_2$=14.8 Hz), 7.78-7.79 (d, 1H, J=7.2 Hz), 7.86 (s, 1H), 7.86-7.88 (d, 1H, J=8.40 Hz), 8.14-8.20 (m, 2H), 8.27-8.29 (d, 1H, J=8.8 Hz) ppm; $^{13}$C NMR (100 MHz, CDCl$_3$): δ 56.29, 60.96, 103.74, 115.91, 117.44, 120.54, 127.55, 127.64, 127.73, 127.86, 129.43, 129.60, 130.35, 137.00, 139.73, 140.74, 140.87, 148.10, 152.21, 153.59 ppm.

Example 7

Synthesis of (Z)-2-(3,5-dimethoxyphenyl)-3-(quinolin-2-yl)acrylonitrile

A mixture of quinolone-2-carboxaldehyde (1.57 g; 0.01 mol) and 2-(3,5-dimethoxyphenyl)acetonitrile (1.77 g; 0.01 mol), sodium methoxide (1.0 gm) in methanol (50 ml) was stirred at reflux temperature for 4 hours. The reaction mass was cooled to room temperature, crushed ice was added to get a solid product. The crude solid was separated by filtration and washed several times with cold methanol (3×5 ml). The isolated light yellow solid was recrystallized from methanol and gave (Z)-2-(3,5-dimethoxyphenyl)-3-(quinolin-2-yl)acrylonitrile as a light yellow crystalline product; MF: $C_{20}H_{16}N_2O_2$, mp: 106° C. -108° C., $^1$H NMR (400 MHz, CDCl$_3$): δ 3.84 (s, 6H), 6.52 (s, 1H), 6.92 (s, 2H), 7.56-7.60 (t, 1H, $J_1$=7.2 Hz, $J_2$=15.2 Hz), 7.73-7.77 (t, 1H, $J_1$=8.0 Hz, $J_2$=15.2 Hz), 7.81 (s, 1H), 7.83-7.85 (d, 1H, J=8.8 Hz), 8.11-8.15 (t, 2H, $J_1$=9.6 Hz, $J_2$=18 Hz), 8.26 (d, 1H, J=8.8 Hz) ppm; $^{13}$C NMR (100MHz, CDCl$_3$) 55.52, 101.63, 104.33, 113.92, 117.59, 126.69, 127.37, 127.49, 127.62, 128.78, 129.29, 129.36, 131.16, 135.16, 135.23, 135.84, 138.33, 148.40, 151.26, 161.31 ppm.

Example 8

Synthesis of (Z)-3-(3,5-dimethoxyphenyl)-3-(quinolin-2-yl)acrylonitrile

A mixture of quinolone-3-carboxaldehyde (1.57 g; 0.01 mol) and 2-(3,5-dimethoxyphenyl)acetonitrile (1.77 g; 0.01 mol), sodium methoxide (1.0 gm) in methanol (50 ml) were stirred at reflux temperature for 4 hours. The reaction mass was cooled to room temperature, crushed ice was added to get a solid product. The crude solid was separated by filtration and was washed several times with cold methanol (3×5 ml). The isolated light yellow solid was recrystallized from methanol and gave (Z)-3-(3,5-dimethoxyphenyl)-3-(quinolin-2-yl)acrylonitrile as a light yellow crystalline product; MF: $C_{20}H_{16}N_2O_2$, mp: 150-152° C., $^1$H NMR (400 MHz, CDCl$_3$): δ 3.85 (s, 6H), 6.52 (s, 1H), 6.85 (s, 2H), 7.58-7.62 (t, 1H, J=8.0 Hz, $J_2$=15.2 Hz), 7.66 (s, 1H), 7.76-7.80 (t, 1H, $J_1$=8.0 Hz, $J_2$=15.6 Hz), 7.92-7.94 (d, 1H, J=8.0 Hz), 8.10-8.12 (d, 1H, J=8.8 Hz), 8.93 (s, 1H), 9.09 (d, 1H, 1.6 Hz) ppm; $^{13}$C NMR (100 MHz, CDCl$_3$): 55.52, 101.63, 104.33, 113.92, 117.59, 126.69, 127.37, 127.49, 127.62, 128.78, 129.29, 129.36, 131.16, 135.23, 135.84, 138.33, 148.40, 151.26, 161.31 ppm.

Example 9

In Vitro Growth Inhibition and Cytotoxicity Formula (II)

In a primary screen, all synthesized compounds were evaluated for their cytotoxic potency at the National Cancer Institute (NCI). The compounds were considered to be active if they reduced the growth of any of the cancer cell lines to 60% or more in at least eight of the cell lines screened. They were then passed on for evaluation in a full panel of 60 different cancer cell lines at five different doses The analogues exhibited good growth inhibition even at nanomolar levels in five dose screening against all the cancer cell lines. Cytotoxic effects of each compound were determined as $GI_{50}$ and $LC_{50}$ values, which represent the molar drug concentration required to cause 50% growth inhibition, and the concentration that kills 50% of the cells, respectively. The results are presented in TABLE 2.

The substitution of 3,4,5-trimethoxyphenyl acrylonitrile moiety on the second position of quinoline (NSC:D-76345211; PNR-4-90) (Z)-3-(quinolin-2-yl)-2-(3,4,5-trimethoxy phenyl)acrylonitrile] exhibited potent growth inhibition on 91% of the cancer cell lines with $GI_{50}$ ranging from 0.033 to 0.943 µM and the average $GI_{50}$ value of this compound on all the cancer cell lines is 0.40 µM. This compound exhibited potent growth inhibition on MDA-MB-435 melanoma cancer cell lines with $GI_{50}$ of 0.033 µM (TABLE 2).

The substitution of 3,5-dimethoxyphenyl acrylonitrile moiety on the second position of quinoline (NSC:D-763448/1 PNR-4-84) [(Z)-3-(quinolin-2-yl)-2-(3-dimethoxyphenyl)acrylonitrile] exhibited potent growth inhibition on 86% of the cancer cell lines with $GI_{50}$ ranging from 0.094 to 0.983 µM and the average $GI_{50}$ value of this compound on all the cancer cell lines is 0.49 µM. This compound exhibited potent growth inhibition on NCI-11522 lung cancer cell lines with $GI_{50}$ of 0.094 µM (TABLE 2).

The substitution of 3,4,5-trimethoxyphenyl acrylonitrile moiety on the third position of quinoline (NSC:D-764126/1; PNR-5-10) [(Z)-3-(quinolin-3-yl)-2-(3,4,5-trimethoxyphenyl)acrylonitrile] exhibited potent growth inhibition on 47% of the cancer cell lines with $GI_{50}$ ranging from 0.227 to 0.911 µM and the average $GI_{50}$ value of this compound on all the cancer cell lines is 2.49 µM. This compound exhibited potent growth inhibition on MDA-MB-435 melanoma cancer cell lines with $GI_{50}$ of 0.227 µM (TABLE 2).

The substitution of 3,5-dimethoxyphenyl acrylonitrile moiety on the third position of quinoline (NSC:D-763449/1 PNR-4-85) [(Z)-3-(quinolin-3-yl)-2-(3,5-dimethoxyphenyl) acrylonitrile] exhibited potent growth inhibition on 81% of the cancer cell lines with $GI_{50}$ ranging from 0.053 to 0.903 µM and the average $GI_{50}$ value of this compound on all the cancer cell lines is 2.21 µM. This compound exhibited potent growth inhibition on MDA-MB-435 melanoma cancer cell lines with $GI_{50}$ of 0.053 µM (TABLE 2).

TABLE 2

Growth Inhibition Concentration and Cytotoxicity Formula (II)

| Panel/cell-line | PNR-4-90 NSC:D-763452/1 Formula (II)(a) | | PNR-4-84 NSC:D-763448/1 Formula (II)(b) | | PNR-4-85 NSC:D-763449/1 Formula (II)(c) | | PNR-5-10 NSC:D-764126/1 Formula (II)(d) | |
|---|---|---|---|---|---|---|---|---|
| | $GI_{50}$ (µM) | $LC_{50}$ (µM) | $GI_{50}$ (µM) | $LC_{50}$ (µM) | $GI_{50}$ (µM) | $LC_{50}$ (µM) | $GI_{50}$ (µM) | $LC_{50}$ (µM) |
| Leukemia | | | | | | | | |
| CCRF-CEM | 0.248 | >100 | 0.332 | >100 | 0.332 | >100 | 1.38 | >100 |
| HL-60(TB) | 0.223 | >100 | 0.27 | >100 | 0.234 | >100 | 329 | >100 |
| K-562 | 0.080 | >100 | 0.353 | >100 | 0.243 | >100 | 0.444 | >100 |
| MOLT-4 | 0.488 | >100 | 0.419 | >100 | 0.378 | >100 | 3.20 | >100 |
| RPM1-8226 | 0.297 | >100 | 0.433 | >100 | 0.332 | >100 | 2.06 | >100 |
| SR | NA | NA | NA | NA | NA | NA | 0.569 | >100 |
| Lung Cancer | | | | | | | | |
| A549/ATCC | 0.375 | >100 | 0.649 | >100 | 0.556 | >100 | 0.680 | >100 |
| HOP-62 | 0.567 | >100 | 0.959 | >100 | 0.793 | >100 | 10.3 | >100 |
| HOP-92 | 0.736 | >100 | 0.542 | >100 | 3.09 | >100 | 0.403 | >100 |
| NCI-H226 | 4.78 | >100 | 10.8 | >100 | 62.2 | >100 | >100 | >100 |
| NCI-H23 | 0.751 | >100 | 0.983 | >100 | 0.747 | >100 | 2.93 | >100 |
| NCI-H322M | 0.718 | >100 | 3.02 | >100 | 0.903 | >100 | 27.4 | >100 |
| NCI-H460 | 0.361 | >100 | 0.339 | >100 | 0.362 | >100 | 2.05 | >100 |
| NCI-H522 | 0.0372 | >100 | 0.094 | >100 | 0.069 | >100 | 0.299 | >100 |
| Colon Cancer | | | | | | | | |
| COLO 205 | 0.198 | 32.7 | 0.374 | >100 | 0.398 | 89.9 | | 9.44 |
| HCC-2998 | 0.61 | >100 | 1.42 | >100 | 1.45 | >100 | 2.01 | >100 |
| HCT-116 | 0.234 | >100 | 0.416 | 47.3 | 0.420 | >100 | 0.464 | >100 |
| HCT-15 | 0.319 | >100 | 0.409 | >100 | 0.455 | >100 | 1.08 | >100 |
| HT29 | 0.24 | >100 | 0.367 | >100 | 0.362 | >100 | 0.421 | >100 |
| KM12 | 0.35 | >100 | 0.425 | >100 | 0.409 | >100 | 0.436 | >100 |
| SW-620 | 0.164 | >100 | 0.357 | >100 | 0.352 | >100 | 0.420 | >100 |

TABLE 2-continued

Growth Inhibition Concentration and Cytotoxicity Formula (II)

| | PNR-4-90 NSC:D-763452/1 Formula (II)(a) | | PNR-4-84 NSC:D-763448/1 Formula (II)(b) | | PNR-4-85 NSC:D-763449/1 Formula (II)(c) | | PNR-5-10 NSC:D-764126/1 Formula (II)(d) | |
|---|---|---|---|---|---|---|---|---|
| Panel/cell-line | $GI_{50}$ (μM) | $LC_{50}$ (μM) | $GI_{50}$ (μM) | $LC_{50}$ (μM) | $GI_{50}$ (μM) | $LC_{50}$ (μM) | $GI_{50}$ (μM) | $LC_{50}$ (μM) |
| CNS Cancer | | | | | | | | |
| SF-268 | 0.835 | >100 | 0.476 | >100 | 0.654 | >100 | 9.17 | >100 |
| SF-295 | 0.277 | >100 | 0.341 | >100 | 0.243 | >100 | 0.556 | >100 |
| SF539 | 0.197 | 14.9 | 0.286 | 8.03 | 0.289 | >100 | 0.361 | >100 |
| SNB-19 | 0.578 | >100 | 0.728 | >100 | 0.614 | >100 | 5.23 | >100 |
| SNB-75 | 0.182 | 98.8 | 0.311 | >100 | 0.224 | >100 | 1.49 | >100 |
| U251 | 0.355 | 90.5 | 0.425 | >100 | 0.374 | >100 | 1.70 | >100 |
| Melanoma | | | | | | | | |
| LOX-IMVI | 0.766 | >100 | 0.61 | >100 | 0.672 | >100 | 0.645 | >100 |
| MALME-3M | na | na | 0.348 | >100 | 0.635 | >100 | 0.691 | >100 |
| M14 | 0.173 | >100 | 0.36 | >100 | 0.310 | >100 | 0.540 | >100 |
| MDA-MB-435 | 0.033 | 60.0 | 0.147 | >100 | 0.053 | >100 | 0.227 | >100 |
| SK-MEL-2 | 0.483 | >100 | 0.522 | >100 | 0.709 | >100 | 1.05 | >100 |
| SK-MEL-28 | 0.518 | >100 | 0.896 | >100 | 1.40 | >100 | 3.27 | >100 |
| SK-MEL-5 | 0.243 | >100 | 0.406 | >100 | 0.249 | >100 | 0.410 | >100 |
| UACC-257 | 0.761 | >100 | Nd | >100 | 12.8 | >100 | Nd | >100 |
| UACC-62 | 0.092 | >100 | 0.449 | >100 | 0.357 | >100 | 0.478 | >100 |
| Ovarian Cancer | | | | | | | | |
| IGROV1 | 0.846 | >100 | 0.958 | >100 | 3.50 | >100 | 3.15 | >100 |
| OVCAR-3 | 0.163 | 54.9 | 0.309 | 34.0 | 0.279 | >100 | 0.263 | >100 |
| OVCAR-4 | 1.43 | >100 | 0.788 | >100 | 1.73 | >100 | 13.8 | >100 |
| OVCAR-5 | 0.580 | >100 | 0.716 | 42.8 | 0.587 | >100 | 3.94 | >100 |
| OVCAR-8 | 0.446 | >100 | 0.659 | >100 | 0.584 | >100 | 3.41 | >100 |
| NCI/ADR-RES | 0.112 | >100 | 0.283 | >100 | 0.224 | >100 | 0.343 | >100 |
| SK-OV-3 | 0.524 | >100 | 0.804 | >100 | 0.576 | >100 | 1.34 | >100 |
| Renal Cancer | | | | | | | | |
| 786-0 | 0.445 | >100 | 0.501 | >100 | 0.484 | >100 | 6.29 | >100 |
| A498 | 0.295 | >100 | 0.275 | >100 | 0.333 | >100 | 0.678 | >100 |
| ACHN | 1.04 | >100 | 0.773 | >100 | 1.19 | >100 | 0.911 | >100 |
| CAKI-1 | 0.068 | >100 | 0.318 | >100 | 0.223 | >100 | 0.346 | >100 |
| RXF 393 | 0.271 | >100 | 0.334 | >100 | 0.297 | >100 | 0.579 | >100 |
| SN12C | 0.627 | >100 | 0.661 | >100 | 0.661 | >100 | 1.94 | >100 |
| TK-10 | 4.69 | >100 | 3.28 | >100 | 17.7 | >100 | 2.55 | >100 |
| UO-31 | 0.762 | >100 | 0.573 | >100 | ad | >100 | 0.580 | >100 |
| Prostate Cancer | | | | | | | | |
| PC-3 | 0.348 | >100 | 0.584 | >100 | 0.506 | >100 | 1.08 | >100 |
| DU-145 | 0.446 | >100 | 0.801 | >100 | 0.505 | >100 | 1.51 | >100 |
| Breast Cancer | | | | | | | | |
| MCF7 | 0.275 | >100 | 0.537 | >100 | 0.333 | >100 | 0.429 | >100 |
| MDA-MB-231/ATCC | 0.943 | >100 | 1.02 | >100 | 1.15 | >100 | 2.83 | >100 |
| HS-578T | 0.689 | >100 | 0.70 | >100 | 0.715 | >100 | 1.31 | >100 |
| BT-549 | 0.315 | >100 | 0.342 | 80.6 | 0.388 | >100 | 1.43 | >100 |
| T-47D | 4.76 | >100 | 1.23 | >100 | 0.628 | >100 | 9.54 | >100 |
| MDA-MB-468 | 0.243 | >100 | 1.50 | >100 | 0.217 | >100 | 0.870 | >100 |

What is claimed is:

1. A compound selected from the group consisting of:

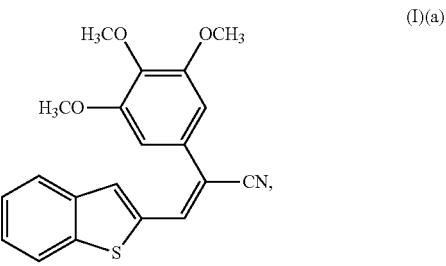

(I)(a)

(I)(b)

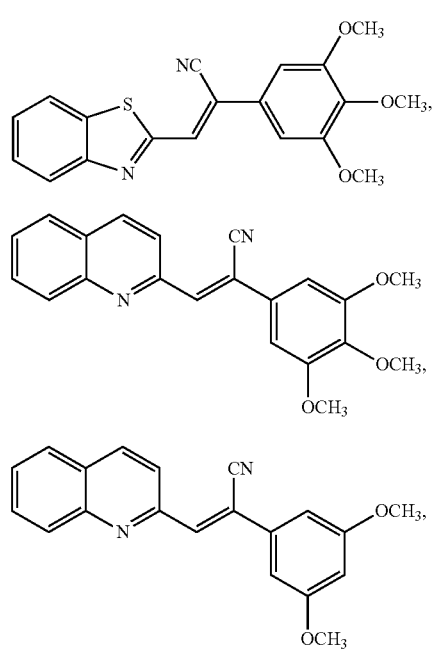
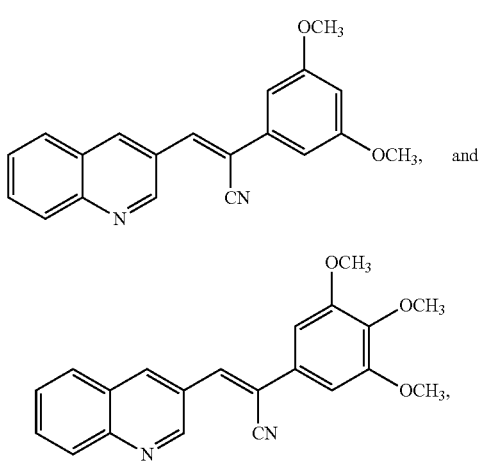
wherein the compound has a 50% growth inhibition ($GI_{50}$) value of less than 100 μm when incubated in vitro with human cancer cell line cultures.
2. A compound of claim 1 in combination with at least one pharmaceutically acceptable excipient.
* * * * *